United States Patent
Blatt et al.

(10) Patent No.: US 7,635,597 B2
(45) Date of Patent: Dec. 22, 2009

(54) DRY REAGENT PARTICLE ASSAY AND DEVICE HAVING MULTIPLE TEST ZONES AND METHOD THEREFOR

(75) Inventors: Joel M. Blatt, Mountain View, CA (US); Michael P. Allen, Los Altos, CA (US)

(73) Assignee: Bayer HealthCare LLC, Tarrytown, NY (US)

( * ) Notice: Subject to any disclaimer, the term of this patent is extended or adjusted under 35 U.S.C. 154(b) by 313 days.

(21) Appl. No.: 10/826,880

(22) Filed: Apr. 19, 2004

(65) Prior Publication Data

US 2005/0196875 A1 Sep. 8, 2005

Related U.S. Application Data

(63) Continuation of application No. 08/512,844, filed on Aug. 9, 1995, now abandoned.

(51) Int. Cl.
*G01N 33/53* (2006.01)

(52) U.S. Cl. .................. 436/518; 436/514; 436/810; 436/808; 435/7.93; 435/7.94; 435/287.7; 422/56; 422/57; 422/58; 422/59; 422/60

(58) Field of Classification Search ............. 422/56–60; 435/287.7; 436/514, 518
See application file for complete search history.

(56) References Cited

U.S. PATENT DOCUMENTS

| | | | |
|---|---|---|---|
| 2,387,244 A | 10/1945 | Compton | |
| 3,419,000 A | 12/1968 | Phillips | |
| 3,620,676 A | 11/1971 | Ward | |
| 3,770,382 A | 11/1973 | Carter et al. | |
| 3,993,451 A | 11/1976 | Verbeck | |
| 4,038,485 A | 7/1977 | Johnston et al. | |
| 4,094,647 A | 6/1978 | Deutsch et al. | ................. 435/4 |
| 4,129,417 A | 12/1978 | White | |
| 4,160,008 A | 7/1979 | Fenocketti et al. | |
| 4,168,146 A | 9/1979 | Grubb et al. | ................. 435/7.92 |
| 4,233,402 A | 11/1980 | Maggio et al. | |

(Continued)

FOREIGN PATENT DOCUMENTS

CA 2019865 A1 1/1991

(Continued)

OTHER PUBLICATIONS

Hawkes, et al., "A Dot-Immunobinding Assay for Monoclonal and Other Antibodies," Analytical Biochemistry, Jan. 1, 1982, vol. 119, No. 1, pp. 142-147.

(Continued)

*Primary Examiner*—Bao-Thuy L Nguyen
(74) *Attorney, Agent, or Firm*—Lerner, David, Littenberg, Krumholz & Mentlik, LLP

(57) ABSTRACT

The present invention relates to a dry reagent assay device having at least one test zone and at least one reference zone, which provides an internal mechanism for assuring correct and reliable assay procedures and reagent qualities. In one embodiment, the present invention relates to an assay device having at least one test zone for detecting at least one analyte in a sample by reacting the sample with a labeled indicator reagent, and a reference zone for receiving unreacted labeled indicator reagent.

10 Claims, 4 Drawing Sheets

U.S. PATENT DOCUMENTS

| | | | |
|---|---|---|---|
| 4,235,601 A | 11/1980 | Deutsch et al. | 436/5.4 |
| 4,248,829 A | 2/1981 | Kitajima et al. | |
| 4,275,149 A | 6/1981 | Litman et al. | |
| 4,281,061 A | 7/1981 | Zuk et al. | |
| 4,301,412 A | 11/1981 | Hill et al. | |
| 4,313,734 A | 2/1982 | Leuvering | |
| 4,315,890 A | 2/1982 | Tamers | |
| 4,361,537 A | 11/1982 | Deutsch et al. | 422/56 |
| 4,366,241 A | 12/1982 | Tom et al. | |
| 4,373,932 A | 2/1983 | Gribnau | |
| 4,376,110 A | 3/1983 | David et al. | 435/5 |
| 4,435,504 A | 3/1984 | Zuk et al. | |
| 4,446,232 A | 5/1984 | Liotta | |
| 4,477,575 A | 10/1984 | Vogel et al. | |
| 4,517,288 A | 5/1985 | Giegel et al. | |
| 4,549,655 A | 10/1985 | Korsythe et al. | |
| 4,552,839 A | 11/1985 | Gould et al. | |
| D282,644 S | 2/1986 | Collister | |
| 4,575,621 A | 3/1986 | Dreifus | |
| 4,594,327 A | 6/1986 | Zuk | |
| 4,595,439 A | 6/1986 | Boger et al. | |
| 4,615,340 A | 10/1986 | Cronenberg et al. | |
| 4,627,445 A | 12/1986 | Garcia et al. | |
| 4,637,403 A | 1/1987 | Garcia et al. | |
| 4,637,978 A | 1/1987 | Dappen | |
| 4,654,310 A | 3/1987 | Ly | |
| 4,673,657 A | 6/1987 | Christian | |
| D292,277 S | 10/1987 | Collister et al. | |
| 4,703,017 A | 10/1987 | Campbell et al. | |
| 4,713,165 A | 12/1987 | Conover et al. | |
| 4,719,338 A | 1/1988 | Avery et al. | |
| D294,807 S | 3/1988 | Stiso et al. | |
| 4,731,726 A | 3/1988 | Allen et al. | |
| 4,734,360 A | 3/1988 | Phillips | |
| 4,740,468 A | 4/1988 | Weng et al. | |
| 4,756,828 A | 7/1988 | Litman et al. | |
| 4,757,004 A | 7/1988 | Houts et al. | |
| 4,774,192 A | 9/1988 | Terminiello et al. | |
| 4,787,398 A | 11/1988 | Garcia et al. | |
| 4,790,979 A | 12/1988 | Terminiello et al. | |
| 4,791,461 A | 12/1988 | Kishimoto et al. | |
| 4,806,312 A | 2/1989 | Greenquist | |
| 4,853,335 A | 8/1989 | Olsen et al. | |
| 4,855,240 A | 8/1989 | Rosenstein et al. | |
| 4,857,453 A | 8/1989 | Ullman et al. | |
| 4,861,711 A | 8/1989 | Friesen | |
| 4,868,108 A | 9/1989 | Bahar | |
| 4,883,688 A | 11/1989 | Houts et al. | |
| 4,913,881 A | 4/1990 | Evers | |
| 4,935,346 A | 6/1990 | Phillips et al. | |
| 4,943,522 A | 7/1990 | Eisinger et al. | |
| 4,943,525 A | 7/1990 | Dawson | |
| 4,945,205 A | 7/1990 | Litman et al. | |
| 4,959,307 A | 9/1990 | Olson | |
| 4,959,324 A | 9/1990 | Ramel et al. | |
| 4,960,691 A | 10/1990 | Gordon et al. | |
| 4,973,549 A | 11/1990 | Khanna et al. | |
| 4,987,085 A | 1/1991 | Allen et al. | |
| 4,995,402 A | 2/1991 | Smith et al. | |
| 4,999,285 A | 3/1991 | Stiso | |
| 4,999,287 A | 3/1991 | Allen et al. | |
| 5,004,582 A | 4/1991 | Miyata et al. | |
| 5,004,583 A | 4/1991 | Guruswamy et al. | |
| 5,006,474 A | 4/1991 | Horstman et al. | |
| D318,331 S | 7/1991 | Phillips et al. | |
| 5,029,583 A | 7/1991 | Meserol et al. | |
| 5,030,558 A | 7/1991 | Litman et al. | |
| 5,035,704 A | 7/1991 | Lambert et al. | |
| 5,036,000 A | 7/1991 | Palmer et al. | |
| D318,811 S | 8/1991 | Caruso et al. | |
| 5,037,614 A | 8/1991 | Makita et al. | |
| 5,039,607 A * | 8/1991 | Skold et al. | 435/7.5 |
| 5,049,487 A | 9/1991 | Phillips et al. | |
| 5,059,394 A | 10/1991 | Phillips et al. | |
| 5,064,618 A | 11/1991 | Baker et al. | |
| 5,075,078 A | 12/1991 | Osikowiez et al. | |
| 5,079,174 A | 1/1992 | Buck et al. | |
| D323,893 S | 2/1992 | Arioka | |
| 5,087,556 A | 2/1992 | Ertinghousen | 435/7.9 |
| 5,089,391 A | 2/1992 | Buechler | |
| 5,091,153 A | 2/1992 | Bachand | |
| 5,096,669 A | 3/1992 | Lauks et al. | |
| 5,104,619 A | 4/1992 | de Castro et al. | |
| 5,110,724 A | 5/1992 | Hewett | |
| 5,114,350 A | 5/1992 | Hewett | |
| 5,120,643 A | 6/1992 | Ching et al. | |
| 5,126,247 A | 6/1992 | Palmer et al. | |
| 5,126,276 A | 6/1992 | Fish et al. | |
| 5,132,086 A | 7/1992 | Allen et al. | |
| 5,135,716 A | 8/1992 | Thakore | |
| 5,141,850 A | 8/1992 | Cole et al. | |
| 5,141,875 A | 8/1992 | Kelton et al. | |
| 5,145,645 A | 9/1992 | Zakin et al. | |
| 5,155,025 A | 10/1992 | Allen et al. | |
| 5,168,042 A | 12/1992 | Ly | |
| 5,171,688 A | 12/1992 | Hewett et al. | |
| 5,173,433 A | 12/1992 | Bachand | |
| 5,174,963 A | 12/1992 | Fuller et al. | |
| 5,177,789 A | 1/1993 | Covert | |
| 5,179,005 A | 1/1993 | Phillips et al. | |
| D334,065 S | 3/1993 | Collister | |
| 5,192,947 A | 3/1993 | Neustein | |
| 5,200,317 A | 4/1993 | Georgevich | |
| 5,200,321 A | 4/1993 | Kidwell | |
| 5,202,268 A | 4/1993 | Kuhn et al. | |
| 5,204,063 A | 4/1993 | Allen | |
| 5,208,147 A | 5/1993 | Kagemow et al. | |
| 5,212,060 A | 5/1993 | Maddox | |
| 5,213,965 A | 5/1993 | Jones | |
| 5,215,886 A | 6/1993 | Patel et al. | |
| 5,218,312 A | 6/1993 | Moro | |
| 5,223,219 A | 6/1993 | Subramanian et al. | |
| 5,223,220 A | 6/1993 | Fan et al. | |
| 5,232,668 A | 8/1993 | Grant et al. | |
| 5,234,813 A | 8/1993 | McGeehan et al. | |
| 5,264,180 A | 11/1993 | Allen et al. | |
| 5,308,775 A * | 5/1994 | Donovan et al. | 436/518 |
| 5,340,539 A | 8/1994 | Allen et al. | |
| 5,354,692 A | 10/1994 | Yang et al. | |
| 5,409,664 A | 4/1995 | Allen | |
| 5,416,000 A | 5/1995 | Allen et al. | |
| 5,451,504 A * | 9/1995 | Fitzpatrick et al. | 435/7.2 |
| 5,569,608 A | 10/1996 | Sommer | |
| 5,580,794 A | 12/1996 | Allen | |
| 5,856,203 A * | 1/1999 | Robinson et al. | 436/518 |
| 2002/0142485 A1 * | 10/2002 | Liu et al. | 436/518 |
| 2002/0160538 A1 * | 10/2002 | Guirguis | 436/539 |

FOREIGN PATENT DOCUMENTS

| | | |
|---|---|---|
| CA | 2020029 A1 | 1/1991 |
| CA | 2028968 A1 | 5/1991 |
| EP | 0182647 A2 | 5/1986 |
| EP | 0330517 A2 | 8/1989 |
| EP | 0357400 A2 | 3/1990 |
| EP | 0421294 A2 | 4/1991 |
| EP | 0430395 A1 | 6/1991 |
| GB | 2090659 A | 7/1982 |
| WO | WO 8300931 A1 | 3/1983 |
| WO | WO 88/08534 * | 11/1988 |
| WO | WO 8808534 A1 | 11/1988 |
| WO | WO 9010869 A1 | 9/1990 |
| WO | WO 9201498 A2 | 2/1992 |

| | | |
|---|---|---|
| WO | WO 9506240 A1 | 3/1995 |
| WO | WO 9746868 A1 | 12/1997 |

OTHER PUBLICATIONS

Sharon, et al., "Detection of Specific Hybridoma Clones by Replica Immunoadsorption of Their Secreted Antibodies," Proc. Natl. Acad. Sci. USA, Mar. 1979, vol. 76, No. 3, pp. 1420-1424.

"Home Cholesterol Testing", Lancet, Dec. 5, 1992, vol. 340, No. 8832, p. 1386.

Van Oudheusden, et al., "A Multilayaer membrane System for Blood Plasma Isolation for Use in Primary Health care", Ann Clin Biochem., 1991, vol. 28, pp. 55-59.

Allen, et al., "Instrument-Free Quantitative Test Systems", Applications of Diagnostics, 1990, pp. 147-176.

Allen et al., "A Noninstrumentated Quantitative Test System and Its Application for Determining Cholesterol Concentration in Whole Blood," Clin. Chem. 1990, vol. 36, No. 9, pp. 1591-1597.

Free et al., "Dry Chemistry Reagent Systems," Lab. Med., Sep. 1984, vol. 15, No. 9, pp. 595-601.

Free et al., "Simple Specific Test for Urine Glucose," Clin. Chem. 1957, vol. 3, No. 3, pp. 163-168.

Comer, "Semiquantitative Specific Test Paper for Glucose in Urine," Anal. Chem. Nov. 1956, vol. 28, No. 11, pp. 1748-1750.

Free et al., "A Simple Test for Urine Bilrubin," Gastroenterology, Jul. 1953, vol. 24, No. 3, pp. 414-421.

Free et al., "Self Testing, An Emerging Component of Clinical Chemistry," Clin. Chem. 1984, vol. 30, No. 6, pp. 829-838.

Balazs, et al., "Use of Test Strips with Colour Meter to Measure Blood-Glucose," Lancet, Jun. 6, 1970, vol. 1, No. 7658, p. 1232.

Free, "Instrumentation for Bedside Information—Progress and Challenges," Pure Appl. Chem., 1982, vol. 54, No. 11, pp. 2063-2073.

Daviaud et al., Clin. Chem. 39:53-59 (1993).

Muller, C. et al., J. Imm. Methods, 37, 185-190, 1980.

Pradella et al., Clin. Chem. 36:1994-1995 (1990).

Roth, J., "Techniques in Immunicytochemistry," Academic Press, pp. 219-284, 1983.

Zuk et al., Clin. Chem. 31:1144-1150 (1985).

* cited by examiner

DRY REAGENT PARTICLE ASSAY AND DEVICE HAVING MULTIPLE TEST ZONES AND METHOD THEREFOR

CROSS REFERENCE TO RELATED APPLICATIONS

This application is a continuation of patent application U.S. Ser. No. 08/512,844, filed on Aug. 9, 1995 now abandoned. The subject matter of this application is also related to U.S. Pat. No. 5,580,794, which was filed as U.S. Ser. No. 08/455,236, which is a continuation of U.S. Ser. No. 08/111,347. All such patents and applications are incorporated herein by reference in their entirety.

FIELD OF THE INVENTION

The present invention relates to a dry reagent assay device having two or more test zones, which provides an internal reference mechanism for assuring correct and reliable assay procedures and reagent qualities.

BACKGROUND OF THE INVENTION

Qualitative and quantitative self-tests have developed gradually over the last half century. Non-instrumented tests have become commercially available using immunochemical reagents on a solid support for diagnostic tests involving HCG, LH, FSH, CKMB, Staphylococcus, and Rubella. Measurement of the hormone HCG to detect pregnancy was among the first of these tests to become commercially successful in the home market. The first home pregnancy test, the e.p.t.™, was introduced in 1977 by Warner-Lambert. The e.p.t.™ used a solution phase chemical reaction that formed a brown ring on the surface of the urine solution in the presence of HCG. The 2 hour long protocol associated with this test was sensitive to vibration and timing, causing false results.

Two additional test systems that appeared in the late 1980s were the LipoScan™ by Home Diagnostics Inc. and the Chemcard™ by Chematics Inc. Both tests measure cholesterol in whole-blood using visual color comparison. Since visual color matching is subjective, these tests do not achieve the quantitative performance necessary for cholesterol testing (Pradella et al, Clin. Chem. 36:1994-1995 (1990)).

For many analytes such as the markers for pregnancy and ovulation, qualitative or semi-quantitative tests are appropriate. There are, however, a variety of analytes that require accurate quantitation. These include glucose, cholesterol, HDL cholesterol, triglyceride, a variety of therapeutic drugs such as theophylline, vitamin levels, and other health indicators. Generally, their quantitation has been achieved through the use of an instrument. Although suitable for clinical analysis, these methods are generally undesirable for point-of-care testing in physicians offices and in the home due to the expense of the instrument.

Recently, a number of non-instrumented methods for measuring analytes use instrument-free quantitation through the use of migration distance, rather than color matching, as the visual signal. In migration distance assays, chemical/biochemical reactions occur as the analyte is wicked through a solid support. During wicking the analyte reacts with a signal-producing reagent and forms a visible signal along the support. The migration distance or the distance of signal border is related to analyte concentration. The operator reads the height of the color bar much the same way one reads a thermometer, and finds the concentration from a calibrated scale.

There are a few migration-type assays commercially available. These include Environmental Test Systems' Quantab™, which measures chloride in swimming pools and during the mixing of concrete, Syva's AccuLevel® for the measurement of therapeutic drugs, and ChemTrak's AccuMeter® for measurement of cholesterol in whole blood. Other companies such as Enzymatics and Crystal Diagnostics have more recently announced the introduction of their Q.E.D.™ and Clinimeter™ technologies to measure, respectively, alcohol in saliva and cholesterol in blood. ActiMed™ discloses a thermometer-type cholesterol assay device in Ertinghausen, U.S. Pat. No. 5,087,556 (1992).

Although these single use, thermometer-type, non-instrumented quantitative devices and non-instrumented color comparison devices for qualitative measurement have shown adequate performance, they have several problems associated with reliability and convenience. First, the colors generated on these devices are not always uniform and sharp. In the case of migration type assays the border is often light in color, unclear and difficult to read. This translates directly into user errors since the user must make a judgment related to the position of the color band border. In the case of non-instrumented pregnancy tests it is sometimes difficult to visually interpret the intensity of the colored spot (especially at HCG concentrations close to the cut-off sensitivity), and interpretation of the result is sometimes a problem. Anytime a non-technical operator is required to make a visual judgment or interpretation, an error is possible, and sometimes, is unavoidable.

Second, the assay protocol for these tests is sometimes difficult and lengthy, taking 15 minutes to 1 hour to obtain a result. Third, these tests often do not have sufficient procedural and reagent references to assure adequate test performance. Fourth and last, non-instrumented devices can only measure single endpoint type tests since enzyme rates or ratiometric analysis of two analytes cannot be measured. Therefore, the menu of potential tests is limited.

As an example of the significance of the problems, a recent article in Clinical Chemistry (Daviaud et al, Clin. Chem. 39:53-59 (1993)) evaluated all 27 home use pregnancy tests sold in France. The authors state, "among the 478 positive urine samples distributed, 230 were falsely interpreted as negative".

In the past, immunoassays were developed for the quantitative and qualitative determination of a wide variety of compounds in a laboratory setting using detailed procedures and expensive instrumentation. Recent developments in immunodiagnostics have resulted in a movement toward more simple approaches to the rapid analysis of clinical samples. The development of solid phase bound reagents has eliminated the need for precipitation in the separation of bound reagents from free reagents. Further advancements in solid phase immunochemistry have resulted in non-instrumented dry reagent strip immunoassays. This configuration allows for the visual qualitative or semi-quantitative determination of analytes in patient samples without the use of an instrument.

There are two basic types of non-instrumented immunoassay configurations. In the first type, or visual color zone type, a signal is generated at a specific zone on the strip where the signal indicates the presence of analyte, and the intensity of the signal indicates the concentration of the analyte in the sample. This type of assay requires visual color interpretation either for the presence of color above a threshold, as in the case of a qualitative test, or the comparison of the color intensity to a color chart, as in the case of a semi-quantitative test. In the second type, the visual signal is produced along the length of a bibulous assay strip. During wicking, the analyte reacts with a signal-producing reagent and forms a visible signal along the support. The migration distance of the signal from the proximal end of the strip is a direct measure of analyte concentration. This type of non-instrumented migration height assay can achieve quantitative results with reasonable performance as disclosed in Zuk et al, Clin. Chem. 31:1144-1150 (1985).

The color zone type of strip immunoassay is usually configured in three ways. First, a one site competitive immunoassay where labeled reagent and analyte compete for binding sites at a discrete zone along a strip where one member of the binding pair is immobilized. Second, a one site inhibition immunoassay where labeled reagent binds substantially all of the sample analyte prior to contact the strip zone where the opposite member of the binding pair is immobilized. Third, a two-site or "sandwich" immunoassay, where the sample analyte has at least two binding sites.

The prior art discloses color zone immunoassays in lateral flow and vertical flow configurations limited to the use of enzymatic signal generating systems. The use of lateral flow wicking strips has focused in the area of enzyme detection in one-site competitive or two-site sandwich configurations, and the use of particle detection has been confined largely to two-site sandwich immunoassays.

There are examples of methods developed where chemical or immunological reactions occurred along the length of a bibulous assay strip. In U.S. Pat. Nos. 4,094,647, 4,235,601 and 4,363,537 Deutsch and Mead disclose a bibulous strip assay with discrete immunochemical reagent zones along its length for conducting specific binding assays. Grubb and Gladd, U.S. Pat. No. 4,168,146, describe an enzyme immunochromatography assay on a bibulous strip wherein a sample containing antigen is wicked through the assay strip, and the antigen in the sample binds to the immobilized antibody and progressively fills the binding sites as a measure of analyte concentration. The antigen containing area is visualized by wetting the strip with an enzyme labeled antibody and developing color with a chromogenic substrate. David, et al., disclose U.S. Pat. No. 4,376,110 that monoclonal antibodies with binding affinities of $10^8$ or greater can be used in forward, reverse and simultaneous two-site sandwich immunoassays.

The lateral wicking immunoassays using colored particle detection for two-site configurations in the prior art are limited to visually interpretation and usually provide only qualitative, or at best, semi-quantitative results. The prior art fails to disclose colored particle detection in lateral wicking devices which use competitive or inhibition immunoassay configurations. Likewise, lateral wicking immunoassay reagent strips designed for use in a quantitative instrument read format are not disclosed in the prior art. Furthermore, the multiple test zone reagent strips of the prior art fail to provide quality reference.

Thus, a need exists in the field of diagnostics for a wicking assay which is sufficiently accurate and reliable to permit point-of-care use by untrained individuals in locations such as the home, sites of medical emergencies, or locations other than a clinic.

SUMMARY OF THE INVENTION

The present invention provides a device for determining the presence of at least one of a plurality of analytes in a sample. The device includes a test zone corresponding to each analyte selected for determining its presence. Each test zone receives and contacts the sample and a labeled indicator reagent corresponding to the selected analyte with a test zone reagent corresponding to the selected analyte. The test zone reagent corresponds to the selected analyte reacting in the presence of the sample and the labeled indicator reagent corresponds to the selected analyte to form a corresponding test zone reaction product and a corresponding test zone detectable response inversely related to the selected analyte level in the sample. The device also includes a reference zone for receiving from each test zone the labeled indicator reagent not reacted with its corresponding test zone reagent and contacting each labeled indicator reagent with a corresponding reference zone reagent. Each reference zone reagent reacts in the presence of the corresponding labeled indicator reagent to form a corresponding reference zone reaction product and a corresponding reference zone detectable response related to each selected analyte level in the sample and related to the corresponding test zone detectable response to establish a substantially constant total detectable response for a pre-determined range of each selected analyte. The device also includes means for combining the detectable responses from the test zones to determine the analyte level in the sample.

The present invention also includes a device for determining the presence of an analyte in a sample. The device includes a first test zone for receiving and contacting the sample and a labeled indicator reagent with a first reagent. The first reagent reacts in the presence of the sample and labeled indicator reagent to form a first reaction product and a detectable response in the first test zone inversely related to the analyte level in the sample. A second test zone receives and contacts the labeled indicator reagent not reacted with the first reagent with a second reagent. The second reagent reacts in the presence of the labeled indicator reagent to form a second reaction product and a detectable response in the second test zone related to the analyte level in the sample and related to the detectable response of the first test zone to establish a substantially constant total detectable response from the test zones for a pre-determined range of the analyte. The device also includes means for combining the detectable responses from the test zones to determine the analyte level in the sample.

The present invention also provides a device for determining the presence of an analyte in a sample which includes a porous member capable of being traversed by the sample. A first zone on the porous member receives and contacts the sample with a labeled indicator reagent diffusively immobilized on the porous member. The labeled indicator reagent reacts in the presence of the analyte to form a mixture. A second zone on the porous member receives and contacts the mixture with a first reagent non-diffusely immobilized on the porous material in the second zone. The first reagent reacts in the presence of the mixture to form a first reaction product and a detectable response in the second zone inversely related to the analyte level in the sample. A third zone on the porous member receives and contacts the remaining mixture with a second reagent non-diffusely immobilized on the porous material in the third zone. The second reagent reacts in the presence of the remaining mixture to form a second reaction product and a detectable response in the third zone related to the analyte level in the sample. The device also includes means for determining the analyte level in the sample from the detectable responses in the second and third zones.

A preferred embodiment of the present invention provides a device for determining the presence of an analyte in a sample which includes a bibulous member capable of being traversed by the sample. A first zone on the bibulous member receives and contacts the sample with a particle-linked antigen diffusively immobilized on the bibulous member. The particle-linked antigen reacts in the presence of the analyte to form a mixture. A second zone on the bibulous member receives and contacts the mixture with an antibody non-diffusely immobilized on the bibulous material in the second zone. The antibody is a specific binding partner to the particle-linked antigen and the analyte, the antibody reacts in the presence of the mixture to bind the particle-linked antigen and express a detectable response in the second zone inversely related to the analyte level in the sample. A third zone on the bibulous member receives and contacts the remaining mixture with an antibody non-diffusely immobilized on the bibulous material in the third zone. The antibody is a first member of a specific binding pair capable of binding to a second member of the specific binding pair on the particle-linked antigen. The second member of the specific binding pair is not a specific binding partner to the analyte. The antibody reacts in the presence of the remaining mixture to bind with the remaining mixture and express a detectable response in the third zone related to the analyte level in the sample. The device also includes means for determining the analyte level in the sample from the detectable responses in the second and third zones.

Another preferred embodiment of the present invention provides a device for determining the presence of an analyte in a sample which includes a bibulous member capable of being traversed by the sample. A first zone on the bibulous member receives and contacts the sample with a particle-linked antibody diffusively immobilized on the bibulous member. The particle-linked antibody reacts in the presence of the analyte to form a mixture. A second zone on the bibulous member receives and contacts the mixture with an antigen non-diffusely immobilized on the bibulous material in the second zone. The antigen is a specific binding partner to the particle-linked antibody. The antigen reacts in the presence of the particle-linked antibody to substantially bind the particle-linked antibody and express a detectable response in the second zone-inversely related to the analyte level in the sample. A third zone on the bibulous member receives and contacts the remaining mixture with an antibody non-diffusely immobilized on the bibulous material in the third zone. The antibody is a first member of a specific binding pair capable of binding to a second member of the specific binding pair on the particle-linked antibody. The second member of the specific binding pair is not a specific binding partner to the analyte. The antibody reacts in the presence of the remaining mixture to bind with the particle-linked antibody and express a detectable response in the third zone related to the analyte level in the sample. The device also includes means for determining the analyte level in the sample from the detectable responses in the second and third zones.

Methods are also provided by the present invention for determining the presence of an analyte in a test sample. One method comprising the steps of: contacting the sample with a porous member having a plurality of zones; transporting the sample sequentially across the plurality of zones and contacting the sample to at least one reagent immobilized in each zone; detecting a response from the contact between the sample and the reagent in at least two zones; and, determining the analyte level in the sample by combining the response from at least two zones.

Another method provided by the present invention determines the level of at least one analyte in a sample. The method comprising the steps of: contacting the sample with an end portion of a bibulous strip having a plurality of zones; wicking the sample to a labeled indicator reagent diffusively immobilized on the bibulous strip; reacting the labeled indicator reagent in the presence of the analyte to form a mixture; wicking the mixture to a first reagent non-diffusely immobilized on the bibulous strip; reacting the first reagent in the presence of the mixture to form a first reaction product and a detectable response inversely related to the analyte level in the sample; wicking the remaining mixture to a second reagent non-diffusely immobilized on the bibulous strip; reacting the second reagent in the presence of the remaining mixture to form a second reaction product and a detectable response related to the analyte level in the sample; and, determining the analyte level in the sample from the detectable responses in the reacting steps with the first and second reagents.

Accordingly, it is an object of the present invention to provide a wicking device which uses competitive and immunoassay configurations for test results which are more accurate and reproducible than in the prior art.

It is a further object of the present invention to provide a assay method using multiple test zones in a single assay to yield accurate quantitative results.

Another object of the present invention is to provide an assay which provides means for quality reference using the signals combined from multiple test zones.

A further object of the invention is to provide a quantitative strip immunoassay based on particle detection.

Other and further advantages, embodiments, variations and the like will be apparent to those skilled-in-the-art from the present specification taken with the accompanying drawings and appended claims.

BRIEF DESCRIPTION OF THE DRAWINGS

In the drawings, which comprise a portion of this disclosure.

DESCRIPTION OF THE PREFERRED EMBODIMENTS

Figure 1:
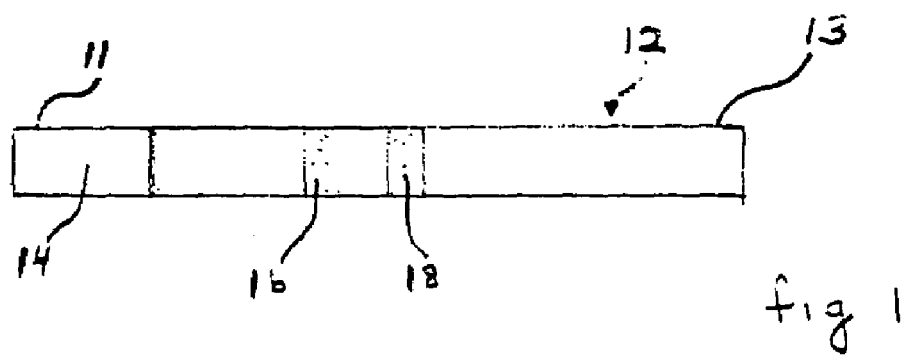
FIG. 1 shows a top surface view of an embodiment having typical structure with three reagent zones that can be used for quantitative and qualitative immunoassays.

The present invention concerns a lateral flow immunoassay strip for use in an instrument system that can produce qualitative or quantitative results. A preferred embodiment of the present invention provides an assay strip including three zones of which two zones are test zones and one of the test zones is a reference zone. A first test zone produces a signal with intensity inversely proportional to analyte concentration and a second test zone acts a a reference and produces a signal that is directly proportional to analyte concentration. The sum of the signals from test zones 1 and 2 is substantially equal at all analyte concentrations. Quantitative or qualitative results are achieved by instrumental reading of color intensity on test zone 1, test zone 2 or both test zones 1 and 2. The results expressed by any one test zone can also be determined as a proportion of the sum of the actual results expressed by both test zones. Quality reference is achieved by instrumental reading of both test zones, the sum of which should be substantially constant within a specified range.

The present invention represents a substantial improvement in the art by providing methods, assay devices and assay instruments which employ (a) a one-step competitive lateral flow strip immunoassay, (b) a one-step inhibition lateral flow immunoassay, (c) a quantitative bibulous strip immunoassay based on particle detection, (d) two or more detection zones for testing, and (e) a reference zone for performing detection tests as a detection zone and perform quality control using the reponses combined from multiple test zones.

The present invention provides an assay which can use specific binding members. A specific binding partner or member, as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies, and antibody fragments, both monoclonal and polyclonal, and complexes thereof, including those formed by recombinant DNA molecules. The term hapten, as used herein, refers to a partial antigen or non-protein binding member which is capable of binding to an antibody, but which is not capable of eliciting antibody formation unless coupled to a carrier protein.

Analyte, as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. Analyte also includes any antigenic substances, haptens, antibodies, macromolecules, and combinations thereof. As a member of a specific binding pair, the analyte can be detected by means of naturally occuring specific binding partners (pairs) such as the use of intrinsic factor protein as a member of a specific binding pair for the determination of Vitamin B12, or the use of lectin as a member of a specific binding pair for the determination of a carbohydrate. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances. In particular, such analytes include, but are not intended to be limited to, ferritin; creatinine kinase MIB (CK-MB); digoxin; phenytoin; phenobarbital; carbamazepine; vancoomycin; gentamicin, theophylline; valproic acid; quinidine; luteinizing hormone (LH); follicole stimulating hormone (FSH); estradiol, progesterone; IgE antibodies; vitamin B2 microglobulin; glycated hemoglobin (Gly. Hb); cortisol; digitoxin; N-acetylprocainamide (NAPA); procainamide; anitbodies to rubella, such as rubella-IgG and rubella-IgM; antibodies to toxoplasmosis, such as toxoplasmosis IgG (Toxo-IgG) and toxoplasmosis IgM (Toxo-IgM); testosterone; salicylates; acetaminophen; hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis Be antigen (HBeAg); antibodies to hepatitis Be antigen (Anti-HBe); thyroid stimulating hormone (TSH); thyroxine (T4); total triiodothyronine (Total T3); free triiodothyronine (Free T3); carcinoembryoic antigen (CEA); and alpha fetal protein (AFP). Drugs of abuse and referenceled substances include, but are not intended to be limited to, amphetamine; methamphetamine; barbiturates such as amobarbital, secpbarbital, pentoaarbital, phenobarbital, and barbital; benzodiazepines such as librium and valium; cannabinoids such as hasish and marijuana; cocaine; fentanyl; LSD; methaqualone; opiates such as heroin, morphine, codeine, hydromorphone, hydrocodone, methadone, oxycodone, oxymorphone, and opium; phenylcyclidine; and propoxyhene. The details for the preparation of such antibodies and the suitability for use as specific binding members are well known to those skilled in the art.

The analyte-analog can be any substance which cross-reacts with the analyte-specific binding member, although it may do so to a greater or lesser extent than does the analyte itself. The analyte-analog can include a modified analyte as well as a fragmented or synthetic portion of the analyte molecule, so long as the analyte-analog has at least one epitope site in common with the analyte of interest. An example of an analyte-analog is a synthetic peptide sequence which duplicated at least one epitope of the whole-molecule analyte so that the analyte-analog can bind to an analyte-specific binding member.

The test sample can be derived from any biological source, such as a physiological fluid, including whole blood or whole blood components including red blood cells, white blood cells, platelets, serum and plasma; ascites; urine; sweat; milk; synovial fluid; raucous; peritoneal fluid; amniotic fluid; percerebrospinal fluid; and other constituents of the body which may contain the analyte of interest. The test sample can be pre-treated prior to use, such as preparing plasma from blood, diluting viscous fluids, or the like; methods of treatment can involve filtration, distillation, concentration, inactivation of interfering compounds, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte. The analyte can be any compound or composition to be detected or measured and which has at least one epitope or binding site.

An assay device for the present invention can have many configurations, several of which are dependent upon the material chosen as the porous member. By "porous" is meant that the material is one through which the test sample can easily pass and includes both bibulous and non-bibulous solid phase materials. In the present invention, the porous member can include a fiberglass, cellulose, or nylon pad for use in a pour and flow-through assay device having multiple layers for multiple assay reagents; a test strip for wicking or thin layer chromatographic capillary action (e.g., nitrocellulose) techniques; or other porous or open pore materials well known to those skilled in the art (e.g., polyethylene sheet material).

In a preferred embodiment, the present dry reagent assay device uses a lateral flow bibulous material with proximal and distal ends, containing at least one central zone along its length. The strip configuration may be of any dimensions which provide the desired number of zones and which permit (a) the desired binding reactions to be completed in a reproducible manner and (b) detection of the reaction indicator to occur. Preferably, the present strip is a total of no more than about 100 mm in length and about 6 mm wide, and more preferably, from about 10 mm to about 40 mm in length and about 1 mm to about 5 mm wide.

The strip is advantageously integrated into any reflectance based instrument, and more preferably, into a disposable electronic assay device, such as that described in U.S. application Ser. No. 08/111,347, previously incorporated by reference.

The bibulous strip can comprise a plurality of zones along its length. The zones can contain diffusively or non-diffusively bound reagents. Each zone can be from about 0.1 mm to about 10 mm wide, more preferably from about 0.25 mm to about 5 mm wide. There will be a minimum of two zones and a maximum of about 10 or more zones, depending on the number of assays to be conducted on one bibulous strip.

In a preferred embodiment, the bibulous strip has three zones along its length. According to this preferred embodiment there are two preferred configurations including a competitive configuration and an inhibition configuration.

The present invention provides an assay method having a competitive type configuration. Referring to FIG. 1, at the proximal end 11 of a strip 12 is a first zone 14, comprising a bibulous material containing a diffusively immobilized, particle-linked antigen. A second zone 16 is separate and distinct from the first zone 14, and is located at some distance toward the distal end 13 of the bibulous strip 12. The second zone 16 includes a bibulous material containing a non-diffusively immobilized antibody capable of binding the particle-linked antigen and free sample antigen. The bibulous material of the second zone 16 can be the same or different from the bibulous material of the first zone 14.

A third zone 18 is separate and distinct from the second zone 16, and is located at some distance toward the distal end 13 of the bibulous strip 12 from the second zone 16. The third zone 18 includes a bibulous material (which may be the same or different from the bibulous materials of the first and second zones 14 and 16) containing a non-diffusively immobilized first member of a specific binding pair, capable of specifically binding to its specific binding partner which is the second member of the specific binding pair on the surface of the particle-linked antigen. This second member of the specific binding pair is not antigenically related to the sample antigen so it will not effectively compete with the antigen to bind to an anti-antigen monoclonal antibody.

The sample is applied to the strip 12 at the application site or first zone 14 which is preferably at the proximal end 11 of the assay strip. The particle-linked antigen is located at or near the application site. The sample containing a sample antigen reconstitutes the dried particle-antigen conjugate by dissolving or dispersing the conjugate, and the mixture of conjugated and free analyte moves via bibulous wicking action to the second zone 16, where the free antigen and particle-conjugated antigen compete for non-diffusively immobilized antibody at this zone. That portion (e.g., from 0% to 100%) of the particle-conjugated antigen which binds to the non-diffusively immobilized antibody is retained in the second zone 16. The antigen-particle conjugate that does not bind to the second zone 16 and migrates to the third zone 18, where substantially all of the portion of the particle-conjugated antigen not retained in the second zone 16 is bound by the non-diffusively immobilized first member of the specific binding pair in the third zone 18.

The present invention provides an assay method having an inhibition type configuration. Again referring to FIG. 1, at the proximal end 11 of the strip 12 is the first zone 14 which includes a bibulous material containing a diffusively immobilized, particle-linked antibody capable of binding sample antigen. The second zone 16 is separate and distinct from the first zone 14, and is located some distance toward the distal end 13 of the bibulous strip. The second zone 16 includes a bibulous material containing a non-diffusively immobilized antigen capable of being bound by the particle-linked antibody. The bibulous material of the second zone 16 can be the same or different from the bibulous material of the first zone 14.

The third zone 18 is separated and distinct from the second zone 16, and is located some distance toward the distal end 13 of the bibulous strip. The third zone 18 includes a bibulous material which may be the same or different from the bibulous materials of the first and second zones 14 and 16 containing a non-diffusively immobilized first member of a specific binding pair capable of specifically binding to its specific binding partner which is the second member of the specific binding pair on the surface of the particle-linked antigen. This second member of the specific binding pair is not antigenically related to the sample antigen so it will not effectively compete with the antigen to bind to an anti-antigen monoclonal antibody.

The fluid sample is applied to the strip at the application site is preferably in the proximal end of the assay strip. The application site is where the particle-linked antibody is located. Sample antigen which may be present in the sample reconstitutes the particle-antibody conjugate and is bound by the conjugate. The bound antigen:antibody-particle complex, as well as unbound antibody-particle complex, are transported or migrate via capillary or wicking action to the second zone 16, where substantially all of the free antibody-particle conjugate is bound by the non-diffusively immobilized antigen. The bound sample antigen:antibody-particle complex migrates through the second zone 16 to the third zone 18, where substantially all of it is bound by the non-diffusively immobilized first member of the specific binding pair.

In the preferred embodiments described above, the amount of a detectable response or signal present at the second zone 16 is an inverse measure of the sample analyte concentration, and the amount of the detectable response or signal at the third zone 18 is a direct measure of the sample analyte concentration. The detectable responsses or signals combined from second and third zones 16 and 18 are approximately constant across the entire range of sample analyte concentration. This total detectable response or signal serves as a reference mechanism for both the assay procedure and reagent quality. Thus, if the total signal is below a specified range, the user is notified of an error. Furthermore, the specific reason for the incorrect assay procedure can be identified. For example, the error can be identified as operation outside the specified temperature and/or humidity range, insufficient sample volume, expired reagents, or the like.

The assay quantitation can be determined by reading the second zone 16, the third zone 18, or both second or third zones 16 and 18. The sample concentration output is a result of a calibration algorithm related to the second zone 16 alone, the third zone 18 alone or both second and third zones 16 and 18. This can result in a more reliable quantitative analyte concentration result. The summation of the detectable responses or signal from second and third zones 16 and 18 to produce a substantially constant total signal regardless of analyte concentration provides a reference mechanism for accurate assay performance.

The above strip configurations are advantageously used in the integrated assay instrument described in U.S. application Ser. No. 08/111,347. Although the chemistry and configurations of the present invention may be used in an integrated assay device, the present invention can be used in any other instrumented reflectance or transmission meter as a replaceable reagent. Thus, the present invention also encompasses integrated assay instruments and analytical assay instruments comprising the present assay device.

The present invention preferably uses particle detection for a detectable response or signal in each test zone related to the level of analyte in the sample. Other means for providing a detectable response in the test zones are suitable for use in the present invention. For example, and not for limitation, the analyte may be labelled with an indicator to measure electrical conductance or the reflectance or absorption of a characteristic light wavelength. As use herein, "indicator" is meant to include all compounds capable of labelling the analyte or conjugate thereof and generating a detectable response or signal indicative of the level of analyte in the sample.

The present assay device and method represents a substantial improvement in the reliability of single-use diagnostic devices utilizing chromatographic strip binding assays for determining the presence or amount of an analyte in a sample, e.g. taken from a medical patient.

The assay devices include a bibulous substrate to which members of specific binding pairs, which may be labeled, are diffusively or non-diffusively immobilized. Non-diffusive immobilization can be conducted by adsorbing, absorbing, crosslinking or covalently attaching a reagent such as a labeled member of a binding pair to the bibulous substrate.

Diffusive immobilization can be conducted by formulating one or more assay reagents to be immobilized. Examples of formulating the reagents include dissolving in a suitable solvent such as water, a $C_1$-$C_4$ alcohol or mixture thereof, along with any desired additives. The resulting formulation is applied to the bibulous material of the assay device in one or more desired locations, and then the bibulous material is dried. Diffusive immobilization allows rapid reconstitution and movement of reagents, whether reacted or unreacted, through the bibulous substrate.

The present invention also includes to a one-step lateral flow assay strip comprising two or more test zones for each analyte and a particle detection system that is quantitatively read by a reflectance type instrument. FIGS. 1-7 show various embodiments of strip configurations suitable for immunoassay devices and methods.

The present immunoassay configurations can measure a wide variety of analytes. The immunoassays can be set up to be either qualitative (e.g., as in the cases of HCG [pregnancy] assays, assays for known metabolites associated with drugs of abuse or for known antigens associated with infectious diseases) or quantitative (e.g., in the case of bone collagen N-telopeptide [NTx; assayed as a marker for bone resorption], theophylline, digoxin, quantitative HCG [ectopic pregnancy], C-reactive protein, CKMB and Troponin).

The present device may be used on-site in the home and in physician's office, or in remote locations in emergency medicine. Therefore, the device may advantageously include sample pre-treatment as previously defined, as well as a sample withdrawal device (e.g., a fingerstick) or any combination thereof. Sample pretreatment can also adjust the pH to within a specified range, reference salt concentration, turbidity and/or viscosity, and/or reduce or remove immunochemical cross-reactants. Each immunoassay configuration shown in FIGS. 1-7 can include sample pre-treatment, including one or more chemical, filtration or separation means, or any combination thereof.

The present invention provides a device which can be used to determine the presence of multiple analytes in a test sample. One test zone corresponds to each analyte selected for determining its presence. Each test zone receives and contacts the sample and a labeled indicator reagent corresponding to the selected analyte with a test zone reagent corresponding to the selected analyte. The test zone reagent corresponds to the selected analyte reacting in the presence of the sample and the labeled indicator reagent corresponding to the selected analyte to form a corresponding test zone reaction product and a corresponding test zone detectable response inversely related to the selected analyte level in the sample.

One reference zone receives the labeled indicator reagent not reacted with its corresponding test zone reagent from all the test zones. The reference zone contacts each labeled indicator reagent with a corresponding reference zone reagent. Each reference zone reagent reacts in the presence of the corresponding labeled indicator reagent to form a corresponding reference zone reaction product and a corresponding reference zone detectable response related to each selected analyte level in the sample and proportionately related to the corresponding test zone detectable response to establish a substantially constant total detectable response for a pre-determined range of each selected analyte. The detectable responses from each test zone are separately combined with the detectable result from the reference zone to determine each selected analyte level in the sample.

Figure 2:
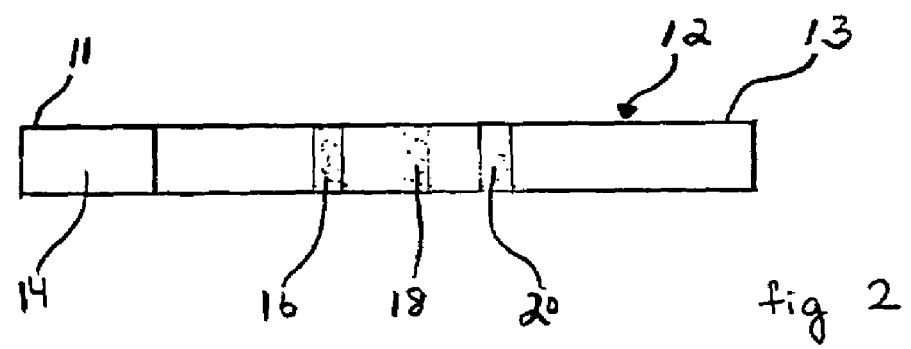
FIG. 2 shows a top surface view of an embodiment having typical structure with four reagent zones that can be used for quantitative and qualitative immunoassays.

Referring again to FIG. 1, a top surface view of an embodiment is illustrated having a typical structure with three zones including two test zones for a single analyte, and FIG. 2 shows a top surface view of a similar device with four zones including three test zones for two analytes. The same reference numerals are used to identify the same elements between the Figures.

In FIG. 1, the first zone 14 of strip 12 is located at or slightly downstream from the sample application site at the prximal end 11 of the strip, and second zone 16, located downstream from the first zone 14, may be either directly adjacent to or separated by a bibulous spacer but in fluid communication with the first zone 14. The third zone 18, located downstream from zones 14 and 16, may be either directly adjacent to the second zone 16 or separated but in fluid communication with the second zone 16. The third zone 18 acts as a reference zone for the second zone 16. As used herein, "fluid communication" refers to a direct or indirect contact of bibulous material which permits a fluid sample to flow from the sample application site or first zone 14 of the device, through the various zones of the device, to the periphery of the device.

FIG. 2 is a similar construction with an additional fourth zone 20, located downstream from zones 14, 16 and 18, which may be either directly adjacent to the third zone 18 or separated but in fluid communication with the third zone 18. The fourth zone 20 acts as a reference zone for each of the second and third zones 16 and 18. All zones are in fluid communication, both with each other and with the sample application site.

The sample application site is preferably in the first zone 14, or alternatively, can be a separate area directly adjacent to and upstream from the first zone 14 (preferably still positioned at the proximate end of the strip). Zones 14, 16, 18, and 20 may be of any dimensions which provide adequate detection of the indicator in the assay(s), and preferably are from about 0.05 cm to about 1.5 cm in length (more preferably about 0.1 cm to about 1.0 cm in length).

The overall dimensions of the strip may be any dimensions which provide adequate spacing and resolution for conducting the assay(s). Preferably, however, the length of the strip is in the range of about 2 cm to about 10 cm (more preferably about 2 cm to about 4 cm) and the width can be about 0.1 cm to about 1.5 cm (more preferably about 0.2 cm to about 0.5 cm). The strips shown in FIG. 1 and FIG. 2 are, for example, about 3 cm long and about 0.3 cm wide.

The strip can be one continuous section of bibulous material or be composed of one, two, three or more sections. Each zone may be a separate bibulous material where each zone is in fluid communication with adjacent zones, or two or more adjacent zones may share a common material, with the other zones being different materials.

The assay strip including each of the zones can be composed of the same or different bibulous materials. The bibulous material permits fluid communication between the various zones, spacers (if present) and sample application site by wicking or capillary action upon application of a fluid sample. Examples of materials that can be used include but are not limited to: cellulose papers such as WHATMAN 1C, 2C, 4C, 31ET, S&S 903C, GB002; membranes such as S&S nitrocellulose, cellulose acetate, regenerated cellulose at pore sizes from 1 µm to 20 µm, Pall nylon at pore sizes of 1µ to 20µ including BIODYNE® A, B, C or IMMUNODYNE® ABC, Gelman ULTRABIND®, Millipore IMMOBILON®; composite papers or membranes made from mixtures of glass fiber, plastic or metal fiber or synthetic or natural mesh or fabric made from cotton, cellulose, polyethylene, polyester or nylon.

Zones 14, 16, 18 and 20 of FIGS. 1 and 2 can contain reagents diffusively or non-diffusively bound including, but not limited to, antibodies, antigens, enzymes, substrates, small molecules, proteins, recombinant proteins, viral or bacterial lysate, receptors, sugars, carbohydrates, polymers like PVA and detergents.

Figure 3:
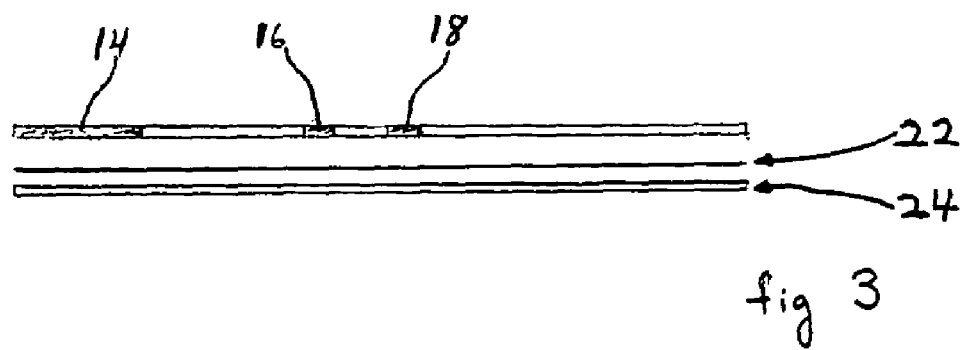
FIG. 3 shows an exploded lengthwise cross section of the embodiment of FIG. 1.
Figure 4:
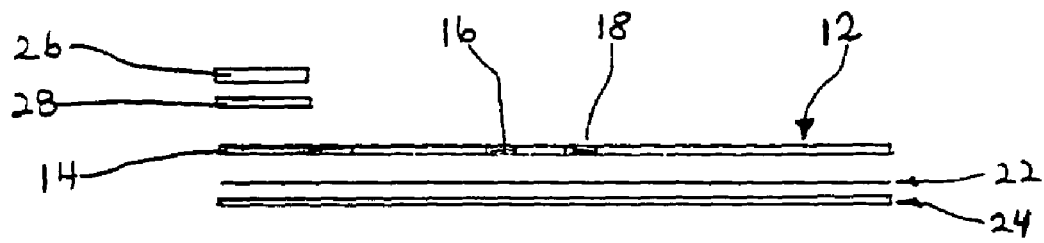
FIG. 4 shows an exploded lengthwise cross section of an embodiment having a typical structure with a sample pretreatment/filtration/separation/blood separation device.
Figure 5:
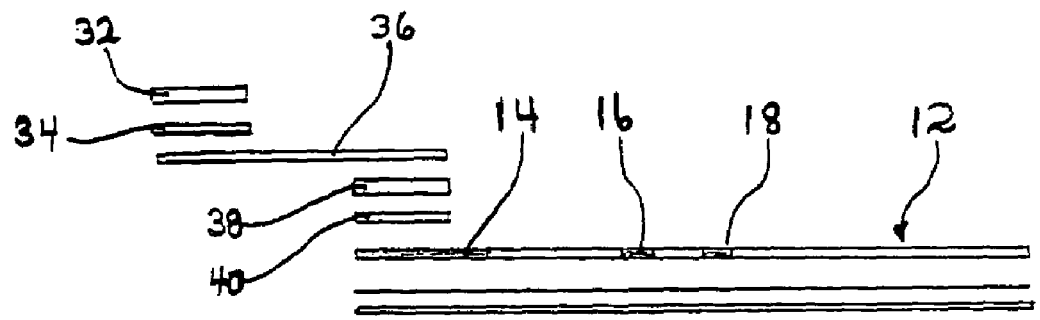
FIG. 5 shows an exploded lengthwise cross section of an embodiment having a typical structure with a sample pretreatment/filtration/separation/blood separation device and a sample transport.

FIGS. 3-5 shows exploded lengthwise cross sections of the embodiment of FIG. 1. The backing 24 in FIGS. 3-5 may provide structural support for the bibulous material. Backing 24 can be of any convenient material that provides support for the assay matrix and is preferably a plastic, such as cellulose acetate, polyester, vinyl or the like, or a synthetic or natural fabric or mesh. Backing 24 has a thickness sufficient to support the assay material, and preferably has a thickness of from about 0.002 inch to about 0.015 inch (more preferably about 0.005 inch to about 0.010 inch thick). However, if the bibulous material is itself sufficiently rigid, or is supported by other mechanical means, then a backing is not necessary.

An adhesive 22 can be interposed between backing 24 and the bibulous material to promote adhesion of these layers. Adhesive 22 can be any double stick adhesive, such as 3M 415, 443, 9460 or the like. Alternatively, a membrane that is cast during manufacturing to a plastic support such as S&S PB-NC can be used. In this case, an adhesive is not necessary.

FIG. 3 shows an exploded lengthwise cross section of the embodiment of FIG. 1 which does not have sample pre-treatment. In this configuration, the sample is introduced at the proximal end 11 of the strip in the area of the first zone 14.

FIG. 4 shows an exploded lengthwise cross section of the embodiment of FIG. 1 with one type of sample pre-treatment. The sample pre-treatment can include any combination of chemical, filtration or separation treatments, including blood separation. The sample treatment zone may be composed of one, two, or several layers of depth filter material 26 (such as glass fiber, metal fiber, synthetic fiber, paper, or natural or synthetic fabric) and a membrane 28 (such as S&S cellulose acetate, nitrocellulose, regenerated cellulose having an average pore size of from about 0.2 µm to about 7 µm, and Nucleopore or Poretics polycarbonate at pore sizes of about 0.2 µm to about 5 µm).

The layers of materials 26 and 28 can contain any number of assay reagents including but not limited to: buffers, salts, proteins, enzymes and/or antibodies (either or both of which may be diffusively or non-diffusively bound to a particle or the bibulous material), polymers, small molecules, or any combination thereof. If red blood cells are to be separated, then layers of materials 26 and 28 function to remove substantially all of the red blood cells from the blood sample, leaving plasma to operate in the assay.

As shown in FIG. 4, sample filtration 26 and 28 is positioned immediately above and in fluid communication with the first zone 14. The sample filtration 26, 28 can be of any dimensions which effectively remove red blood cells from a whole blood sample to be assayed, and are preferably from about 0.2 to about 1 cm in length. The sample filtration can be secured with adhesive or be held in place by the instrument housing. The adhesive for affixing the sample filtration means in place may be any adhesive, such as epoxy, hot melt glue, or the like, or an adhesive tape such as that made by the 3M company.

FIG. 5 shows an exploded lengthwise cross section of the embodiment of FIG. 1 with a second type of sample pre-treatment and transport means. The sample treatment in the device of FIG. 5 can include any combination of chemical, filtration or separation means, including blood separation means. The sample treatment and transport device of FIG. 5 includes a sample application zone at filter 32, a membrane 34, a transport mesh 36, a second filter 38 and a membrane 40.

The filter 32 can be composed of one, two, three or more layers of any bibulous material, preferably a depth filter such as glass fiber, metal fiber, synthetic fiber, paper, or natural or synthetic fabric. Filter 34 can be one or several layers and is composed of any microporous membrane such as S&S cellulose acetate, nitrocellulose, regenerated cellulose at pore sizes from about 0.2 µm to about 7 µm, Nucleopore or Poretics polycarbonate at pore sizes of about 0.2 µm to about 7 µm.

Although filters 32 and 34 are shown in FIG. 5, one or both of these layers may not be necessary and can be excluded. In the case where both filter layers 32 an 34 are excluded, the sample will be applied directly to the transport layer 36.

The sample transport layer 36 is designed to accept the sample, either directly or through the filter layers 32 and 34, and move it horizontally to the area of filter 38. This sample movement may take from about 2 seconds to about 10 minutes, preferably from about 2 seconds to about 5 minutes, and more preferably from about 5 seconds to about 2 minutes.

The sample transport is composed of any bibulous material including, but not limited to, fabric or mesh that is woven or cast, synthetic or natural, and made of cotton, nylon, polyester, polypropylene, polyethylene or the like; paper such as Whatman 31ET or 3MM; glass fiber such as Whatman GFA, GFD, S&S 3362 or 32; plastic fiber, metal fiber and/or any synthetic membrane. The sample transport area can be untreated, or may have diffusively or non-diffusively immobilized therein one or more reagents such as stabilizing proteins, detergents, anticoagulants like heparin or EDTA, precipitating reagents, salts, proteins, enzymes, antibodies, enzyme-particle conjugates, antibody-particle conjugates, antigen-particle conjugates, red cell agglutinating agents like wheat germ lectin or anti-human RBC, polymers and/or small molecules.

The sample transport layer/zone 36 has dimensions sufficient to permit any desired sample pre-treatment without adversely affecting assay reactions and indicator measurements, but is preferably about 0.5 cm to about 5 cm (more preferably about 1 cm in length) in length and about 0.1 to about 1.5 cm (more preferably about 0.2 to about 0.5 cm) in width.

The filter 38 can be composed of one, two, three or more layers of any bibulous material, preferably a depth filter such as glass fiber, metal fiber, synthetic fiber, paper, or natural or synthetic fabric. Filter 40 can be one or several layers and is composed of any microporous membrane such as S&S cellulose acetate, nitrocellulose, regenerated cellulose at pore sizes from about 0.2 µm to about 7 µm, Nucleopore or Poretics polycarbonate at pore sizes of about 0.2 µm to about 5 µm. Although filters 38 and 40 are shown in FIG. 5, one or both of these layers may not be necessary and can be excluded. In the case where both filter layers 38 and 40 are excluded then the sample will be transported directly from the transport layer 36 to the first zone 14. All of the sample treatment and transport materials 32, 34, 36, 38, and 40 are in fluid communication with each other and with the first zone 14.

If the device is used for blood separation then it will function to remove substantially all of the red cells from the blood sample, leaving plasma to operate in the assay. The red cells can be substantially removed by filters 32 and 34 prior to the sample contacting the transport mesh or the red cells can be removed by filters 38 and 40 in which case the whole blood will travel on the transport layer. In a preferred embodiment, filters 32 and 34 are absent and sample blood or urine or any other body fluid is applied directly to the transport layer and sample treatment, filtration and/or blood separation occurs at filters 38 and 40.

Filters 32, 34, 38, and 40 have dimensions sufficient to permit any desired sample pre-treatment without adversely affecting assay reactions and indicator measurements, but preferably are about 0.2 cm to about 2 cm (more preferably about about 0.25 to about 0.75 cm) in length and about 0.1 to about 1.5 cm (more preferably about 0.2 to about 0.5 cm) in width. The components of the sample treatment means and transport means of FIG. 5 can be secured with adhesive or held in place by a rigid housing. The adhesive can be any convenient adhesive including epoxy, hot melt glue, or the like, or may be an adhesive tape such as those made by 3M company.

Figure 6:
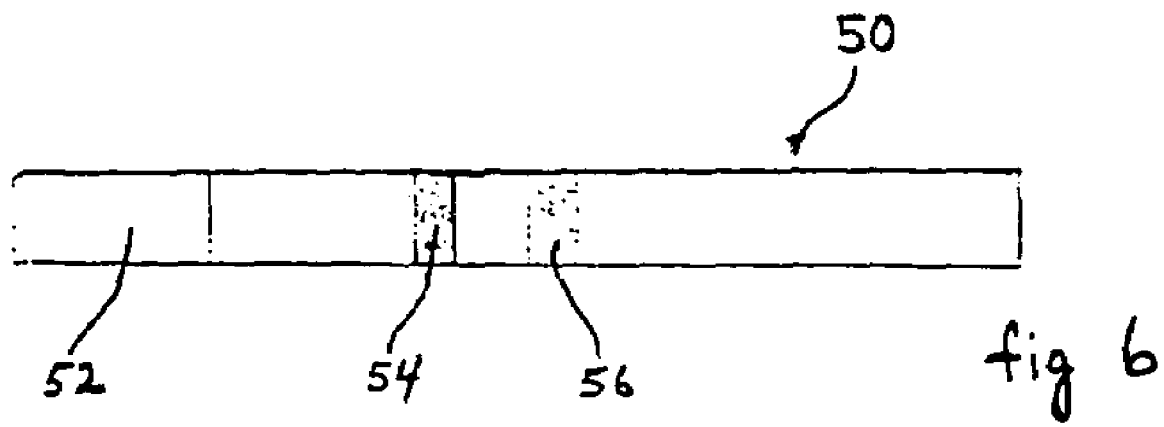
FIG. 6 shows the top surface view of one embodiment of the N-telopeptide (NTx) assay strip.
Figure 7:
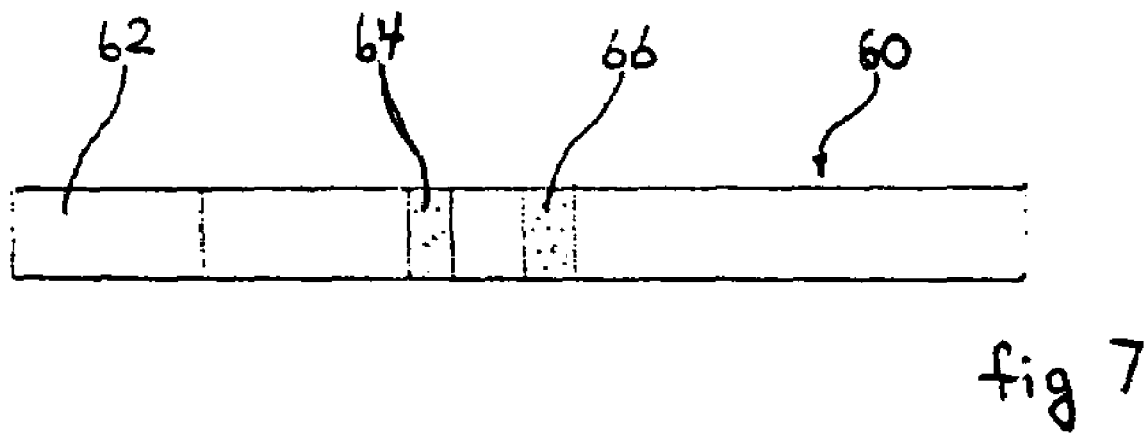
FIG. 7 shows the top surface view of a second embodiment of the N-telopeptide (NTx) assay strip.

Referring now to FIGS. 6 and 7, each of these immunoassay formats can have a sample treatment means and/or a transport means as described for the assay devices in FIGS. 4 and 5. Alternatively, they may have a sample treatment means as described for the assay device in FIG. 3.

FIGS. 6 and 7 show two embodiments of a quantitative assay to measure the concentration of the crosslinked bone collagen N-telopeptide (NTx) in urine, whole blood, plasma or serum. NTx is a product of bone resorption and is known to be present in urine and blood. The concentration of NTx is a direct measure of the rate of bone resorption and is a useful marker for (a) the onset of osteoporosis and (b) monitoring the progress of therapy for osteoporosis. Although NTx is shown as an example assay according to the present invention, it is understood that any analyte can be quantitatively or qualitatively measured.

The assay strips of FIGS. 6 and 7 each have two test zones. The two-test zone design provides improved performance in quantitative assays and improved reliability, since the sum of the signals from both test zones is substantially constant regardless of the analyte/antigen concentration, thus providing a robust quality reference and assuring accurate assay operation.

FIG. 6 is a top surface view of an inhibition type immunoassay configuration, a preferred embodiment of the present invention. In the assay strip 50, zone 52 contains a diffusively bound anti-NTx antibody (or any other antibody), conjugated to colloidal gold, colored latex beads or an enzyme. The diffusively immobilized anti-NTx-particle conjugate can also be located on filters 26 or 28 of the device of FIG. 4 or on filters 32, 34, 38 or 40 or transport layer 36 of the device of FIG. 5.

The antibody can be monoclonal (e.g., derived from fusion of spleen cells from an immunized mouse with a suitable immortal cell line in accordance with known methods; see *Kohlstein and Milner,* 1975) or polyclonal (e.g., prepared from any suitably immunized animal species in accordance with known methods).

A preferred embodiment uses conjugates of anti-NTx antibody to particles of colloidal gold, or to blue or black latex beads. Particles can be from about 5 nm to about 2000 nm in diameter (more preferably from about 5 nm to about 500 nm in diameter).

Diffusive immobilization can be conducted by formulating the assay reagent(s) to be immobilized (e.g., by dissolving in a suitable solvent such as water, a $C_1$-$C_4$ alcohol or mixture thereof, along with any desired additives), applying the resulting formulation to the bibulous material of the membrane, filter or transport layer in the desired location(s), and drying the material. Suitable additives may include detergents, proteins, blocking agents, polymers, sugars or the like. Alternatively, the additive(s) and assay reagent(s) may be applied to the membrane, filter or transport layer by precoating with a "blocking agent", water soluble polymer, sugar or detergent, followed by depositing the conjugate or conjugate formulation and drying the material.

Zone 54 is the first test zone of strip 50. Zone 54 contains non-diffusively bound NTx, NTx-macromolecule conjugate or NTx-particle conjugate. NTx is conjugated to a macromolecule or particle to help in the immobilization of the NTx peptide to the membrane (bibulous material) surface. Suitable macromolecules which can be used for NTx conjugation include any large molecule capable of adsorption or covalent binding to the membrane, including but not limited to: bovine serum albumin (BSA), keyhole limpet hemocyanin (KLH), immunoglobulin G (IgG), mouse IgG, bovine gamma globulin (BGG), lactalbumin, polylysine, polyglutamate, polyethylenimine, or aminodextran. Suitable particles which can be used for NTx conjugation can include particles of about 1-20 µm in diameter, including but not limited to, latex particles, microcapsules, liposomes or metal sol particles.

Non-diffusive immobilization can be accomplished by covalently attaching, adsorbing or absorbing the NTx, NTx-protein conjugate or NTx particle conjugate to the membrane. Suitable membranes for adsorption or absorption include, but are not limited to, S&S nitrocellulose and cellulose acetate at pore sizes from 0.45 µm to 12 µm, and Pall nylon at pore sizes of 0.45 µm to 20 µm (such as BIODYNE A, B, and C). Suitable membranes for covalent attachment include, but are not limited to, membranes such as Millipore IMMOBILON®, Gelman ULTRABIND® and Pall IMMUNODYNE® ABC. Alternatively, the antigen, antigen-protein conjugate or antigen-particle conjugate can be covalently attached to the membrane by chemically activating the membrane or paper prior to applying a solution or formulation of antigen/conjugate. Covalent attachment of the NTx peptide to the membrane occurs through a linkage to the primary amine on the NTx molecule.

Zone 56 is the second test zone of strip 50. Zone 56 contains a non-diffusively bound member of a specific binding pair capable of binding to a complementary member of the specific binding pair which is not related to the sample analyte/antigen on the surface of the particle-linked antibody.

For example, if the particle-linked antibody is a mouse monoclonal antibody, then the non-diffusively immobilized complementary binding partner in zone 56 can be any anti-mouse polyclonal or monoclonal antibody, including but not limited to: goat-anti-mouse, sheep-anti-mouse, cow anti-mouse, rabbit-anti-mouse, monoclonal rat anti-mouse or any other anti-mouse species antibody.

Alternatively, a generic binding partner such as Protein A, Protein G or Protein A/G (e.g., obtained from Pierce) can be non-diffusively immobilized at zone 56, as long as it binds the particle-antibody conjugate. Lectins can also be immobilized at zone 56, provided that the particle-antibody conjugate can be bound at this zone. Biotin, avidin or streptavidin can be linked to particle or to the particle-linked antibody, and the complementary binding partner may then be non-diffusively immobilized at zone 56.

For example, if biotin is conjugated to the particle along with the antibody, thus producing an anti-NTx-particle-biotin conjugate, then avidin or streptavidin can be non-diffusively immobilized at zone 56 and used to capture particles not bound in zone 54. Any non-human antigen, including proteins or small molecules such as dinitrophenol, known dinitrophenyl group-containing molecules or fluorescein can be co-conjugated with anti-NTx to the particle. The complementary antibody can then be immobilized to zone 56, the requirement being that the particle conjugate not bound in zone 54 is substantially all captured (bound) in zone 56 in the assay.

In the assay operation of FIG. 6, the sample is introduced to the proximal end of the assay strip in the area of the particle-linked antibody conjugate zone 52. The sample can be applied directly, or can be pre-treated, filtered, and/or separated as described above. The fluid sample (sample antigen, in this case NTx) then reconstitutes the particle-antibody (particle-anti-NTx) conjugate, and any antigen in the fluid sample is bound by the conjugate in zone 52. The particle-antibody conjugate is applied in excess, such that most of the antigen is bound by the conjugate.

The bound antigen:antibody-particle complex (NTx:anti-NTx-particle), as well as unbound antibody-particle (anti-NTx-particle) conjugate, migrate from zone 52 via capillary action to zone 54, where substantially all of the free antibody-particle conjugate is bound by the non-diffusively immobilized antigen (NTx) at this site. The antigen:antibody-particle complex cannot bind to the non-diffusively immobilized antigen at zone 54 since the binding sites are occupied by sample antigen. Consequently, the antigen:antibody-particle complex migrates via capillary action to zone 56 and is substantially all bound by the non-diffusively immobilized complementary member of the specific binding pair immobilized at this site.

At zero sample antigen concentration, the binding sites on the particle-antibody conjugate are free, and the particles are mostly bound at zone 54, where a dark color is produced. At very high sample antigen concentrations, the binding sites on the particle-linked antibody are mostly occupied, and the particles move past zone 54 and are substantially all bound at zone 56. Intermediate concentrations of sample antigen result in a predictable response relative to the bound particle signals at zones 54 and 56. In general, low sample concentrations result in high signal in zone 54 and low signal in zone 56. As analyte/antigen concentration increases, the signal in zone 54 becomes progressively lower, and the signal in zone 56 becomes correspondingly higher. The total signal, which is the sum of signal from zones 54 and 56, remains substantially constant across the entire concentration range. This provides a reliable quality reference for the assay result, since the sum of the signals must stay within a specified range. Otherwise, an assay failure is indicated.

Assay calibration and sample quantitative measurement can be achieved using zone 54 alone, zone 56 alone or both zones 54 and 56. Under certain conditions, one test zone may produce better performance in a particular analyte/antigen concentration range, and the other test zone may produce better performance in a different analyte/antigen concentration range. In this case, a hybrid calibration can be done that uses the optimal calibration range of each zone. Thus, the present two-test zone measurement provides substantial improvements over previously described methods.

FIG. 7 is a top surface view of a competitive-type immunoassay configuration, another preferred embodiment of the present invention. In the assay strip 60, zone 62 contains diffusively bound NTx (or other sample antigen) conjugated to colloidal gold, colored latex beads or an enzyme. The NTx can be coupled directly to the particle. Alternatively, NTx can be coupled indirectly to the particle through the macromolecule moiety of a macromolecule-NTx conjugate. The macromolecule used for NTx conjugation can be any large molecule capable of adsorption or covalent binding to the particle, including but not limited to: bovine serum albumin (BSA), keyhole limpet hemocyanin (KLH), immunoglobulin G (IgG), mouse IgG, bovine gamma globulin (BGG), lactalbumin, polylysine, polyglutamate, polyethylenimine, or aminodextran.

A preferred embodiment uses conjugates of NTx to particles of colloidal gold, or to blue or black latex beads. Particles can be from about 5 nm to about 2000 nm in diameter (more preferably from about 5 nm to about 500 nm in diameter).

The NTx-particle conjugate can also be diffusively immobilized on filters 26 or 28 of the device of FIG. 4 or on filters 32, 34, 38 or 40 or transport layer 36 of the device of FIG. 5. Diffusive immobilization can be accomplished as described above.

Zone 64 is the first test zone of strip 60. Zone 64 contains non-diffusively bound anti-NTx. Non-diffusive immobilization can be accomplished by covalent attachment or adsorption of the anti-NTx to the membrane as described above. Alternatively, anti-NTx can be conjugated to another protein, and this conjugate is then adsorbed to the membrane. Adsorption can be accomplished using membranes including, but not limited to, S&S nitrocellulose and cellulose acetate at pore sizes from 0.45 μm to 12 μm, and Pall nylon at pore sizes of 0.45 μm to 20 μm (such as BIODYNE A, B, and C). Covalent attachment can be accomplished using membranes such as Millipore IMMOBILON®, Gelman ULTRABIND® or Pall IMMUNODYNE® ABC, or by chemically activating the membrane or paper prior to contacting the antibody with the membrane or paper.

Zone 66 is the second test zone of strip 60. Zone 66 contains a non-diffusively bound member of a specific binding pair such as an antibody or an antigen which is not immunologically related to the sample analyte/antigen, avidin, biotin, Protein A or G, lectin or the like) which binds to a complementary member of the specific binding pair on the surface of the particle-linked antigen. For example, if the particle is linked to both antigen and protein (e.g., an antigen-macromolecule-particle conjugate), then an antibody to that protein can be non-diffusively immobilized in zone 66.

Furthermore, for example, if NTx is conjugated to mouse IgG, and the particle is linked to this conjugate (NTx-mouse IgG-particle), then any anti-mouse antibody can be non-diffusively immobilized at zone 66. Any protein carrier can be used to conjugate to NTx, and the corresponding antibody (to the protein carrier) is then non-diffusively immobilized to zone 66.

Alternatively, any generic binding partner such as Protein A, Protein G or Protein A/G (e.g., obtained from Pierce) can be non-diffusively immobilized at zone 66 as long as it binds the particle-antigen conjugate. Lectins can also be immobilized at zone 66, provided that the particle-antigen conjugate can be bound at this zone.

Biotin, avidin or streptavidin can be conjugated to the particle-linked antigen, and the complementary binding partner can then be non-diffusively immobilized in zone 66. For example, if biotin is conjugated to the particle along with the antigen (in this case NTx), thus producing a biotin-particle-NTx conjugate, then avidin or streptavidin can be non-diffusively immobilized in zone 66.

Any non-human antigen, including proteins or small molecules such as dinitrophenol, known dinitrophenyl group-containing molecules or fluorescein, can be co-conjugated with NTx to the particle, and the complementary antibody can be immobilized in zone 66, the requirement being that the particle conjugate that is not bound in zone 64 is substantially all captured (bound) in zone 66 in the assay.

In the assay operation, the sample is introduced to the proximal end of the assay strip in the area of the particle-linked antigen conjugate zone 62. The sample can be directly applied, or alternatively, it can be pre-treated, filtered, and/or separated as described above. The fluid sample (which may contain antigen, in this case NTx) then reconstitutes the particle-antigen (particle-protein-NTx) conjugate, and the mixture of particle-protein-NTx and free analyte (NTx) moves via capillary migration or bibulous wicking action from zone 62 to zone 64, where the free antigen and particle-conjugated antigen compete for non-diffusively immobilized antibody. The antigen-particle conjugate that does not bind to zone 64 migrates to zone 66 and is substantially all bound by the non-diffusively immobilized member of the specific binding pair immobilized at this site.

At zero sample analyte/antigen concentration, the particle-antigen conjugate is mostly bound in zone 64, resulting in a dark color being produced in this zone. At very high sample analyte/antigen concentrations, the analyte/antigen occupies most of the binding sites of zone 64, causing the particle-linked conjugate to move past zone 64 to zone 66, where it is substantially all bound. Intermediate concentrations of sample analyte/antigen result in a predictable response relative to the bound particle signals in zones 64 and 66.

In general, low analyte/antigen concentrations result in high signal in zone 64 and low signal in zone 66. As sample analyte/antigen concentration increases, the signal in zone 64 becomes progressively smaller, and the signal in zone 66 becomes correspondingly higher. The total signal or detectable response (i.e., the sum of the signals from zones 64 and 66), remains substantially constant regardless of the analyte/antigen concentration (e.g., across the entire concentration range of from 0 to about 100 mM). This provides a reliable assay result and quality reference since the sum must stay within a specified range, otherwise an assay failure is indicated.

Assay calibration and sample quantitative measurement can be achieved using zone 64 alone, zone 66 alone or both zones 64 and 66. Under certain conditions, one test zone may produce better performance in a particular analyte/antigen concentration range, and another test zone may produce better performance in a different analyte/antigen concentration range. In this case, a hybrid calibration can be done that uses the optimal calibration range of each zone. Thus, the present two-test zone measurement provides substantial improvements over previously described methods.

The present test strip may be advantageously used in an instrument which reads the signals in zones 64 and 66. Thus, the indicator signals need not be visually detectable.

Having generally described the present invention, a further understanding can be obtained by reference to the following specific examples, which are provided herein for purposes of illustration only and are not intended to be limiting of the present invention. Unless otherwise specified, temperatures are in degrees Centigrade and percents are weight percents.

EXAMPLE 1

The devices of the embodiments shown in FIGS. 1-7 are quantitative or qualitative immunoassay strips. The assay strips shown in these embodiments can be configured by one of two assembly methods.

In a first strip assembly method, the strip is composed of several separate bibulous membrane sections in fluid communication by lamination to a plastic strip. The reagents can be diffusively or non-diffusively immobilized to the membrane prior to lamination. Alternatively, the reagents can be immobilized after lamination.

For convenience, the assay strips are constructed in bulk in a card form with the discrete assay zones forming lines along the length of the card. Each card can be of any convenient size, depending only on the length of the assay strip and the number of assay strips desired. For example, if the assay strip (as shown in FIG. 1) is 6 cm long and 0.5 cm wide, then the card can be 6 cm by 10 cm (20×0.5 cm), thus providing 20 strips. Two sizes of strips were used in the examples below. For a strip size of 6 cm long by 0.5 cm wide, the card was 6 cm by 10 cm (yielding 20 strips); for a strip size of 3 cm long by 0.3 cm wide, the cards were 3 cm by 6 cm (allowing 20 strips).

In a second strip assembly method, the strip is one continuous material that may optionally be laminated or cast to a plastic support. The reagents are diffusively or non-diffusively immobilized to a continuous assay strip, and are applied to the strip using a process that "prints" the reagents in discrete zones along the length of the strip. The assay strips may be constructed in bulk in a card form in accordance with the first strip assembly method described above.

The following strip assembly and reagent immobilization methods were used in the construction of the present invention.

One method of constructing a strip assembly for the present invention laminated the membrane or paper to a plastic backing by joining the membrane or paper assay matrix to a sheet of polyvinyl acetate (0.01" thick) using a double-stick adhesive or a transfer adhesive. This is illustrated in FIGS. 3-5.

A card of polyvinyl acetate sheet (0.01" thick) was cut to about 6 cm by 10 cm (or 3 cm by 6 cm). The size of the card varied, depending on the desired assay card size. The polyvinyl acetate backing was marked with pencil lines along the length at appropriate positions indicating the location of the various assay strip zones. Double stick adhesive, such as 3M 415 to the polyvinyl acetate, was applied so as to cover the surface with the pencil lines, and firm pressure was applied with a roller assembly making sure to eliminate the formation of bubbles. The release liner of the double-stick adhesive was removed and the membrane or paper assay sections applied to the correct location, guided by the pencil lines, and firm pressure was applied with a roller assembly making sure to eliminate bubbles. Care was taken to ensure that each section of the bibulous assay matrix was in fluid communication with its neighbor. Finally, individual assay strips were cut, each 0.5 cm wide (or 0.3 cm) along the length of the card, resulting in assay strips 6 cm long by 0.5 cm wide (or 3 cm long by 0.3 cm wide). This was accomplished using a die cutter or a standard paper cutter.

A non-diffusive immobilization was accomplished using a variety of methods. In a preferred method, nitrocellulose or nylon membrane (pore sizes of 0.45 μm to 12 μm) was incubated with a protein, protein-hapten conjugate, peptide, small molecule or the like (immobilization compound) to be non-diffusively immobilized, in 50 mM sodium phosphate, pH 7, for 60 minutes. The membranes were then washed twice in 50 mM sodium phosphate pH 7, 0.1 M NaCl (PBS) for 15 minutes and preserved in 5 mg/mL BSA, 1% sucrose solution for 10 minutes. Drying was done at 50° C. for 15 minutes or until dry.

In a second non-diffusive immobilization method, an applicator (e.g., a fountain pen, a pad printer, pipette, air brush, inkjet print head or the like) was used to accurately measure the reagents onto appropriate zones of the assay matrix. In this case, the immobilization compound was diluted to between 0.01 mg/mL and 10 mg/mL with 50 mM phosphate, pH 7, and introduced into the application device. The application device was then positioned above the appropriate assay zone and the immobilization material was coated onto the assay matrix. The strips were washed using PBS and preserved with BSA/sucrose prior to drying, or they may not be washed or preserved. The assay membrane was then dried at 50° C. for 15 minutes or until dry. This method provides flexibility in "printing" reagents in a referenceled manner at any location along the assay strip.

In a third method, the immobilization compound can be covalently coupled to latex microparticles of about 1-20 μm and these particles are drawn into the membrane matrix using suction or pressure. The microparticle method is accomplished by first covalently immobilizing the desired protein to microspheres with carboxyl functional groups as follows: To a suspension of 10 μm microspheres-COOH (e.g., Bangs Laboratories stock #P0100000CN) add 1.1 molar equivalents (relative to the COOH groups on the bead surface) of 1-ethyl-3-(dimethylaminopropyl)carbodiimide (EDAC, Sigma E 0388) and 1.1 molar equivalents of N-hydroxysuccimimide (NHS, Pierce 24500) in 0.1 M sodium phosphate, pH 7.0, at room temperature with stirring for 30 minutes. Add this mixture to a stirring solution of the desired protein in 0.1 M sodium phosphate, pH 7.0, (the protein is at a 10 fold molar excess over the COOH functional groups on the bead surface). Allow to react for 2 hours at room temperature and then purify by centrifuging, followed by washing and dialysis. The microparticles now have the desired protein covalently immobilized. The protein-particle suspension is then mixed and 2-10 μL is picked up using a pipette. The membrane or paper assay strip is placed on a sintered glass filtration platform with vacuum and the bead-protein suspension is applied from the pipette across the assay strip in the correct location. The vacuum pressure draws the conjugated beads into the matrix of the membrane or paper where they are mechanically non-diffusively immobilized. Alternately these beads can be applied to the membrane using an air brush or inkjet type print head.

A fourth type of non-diffusive immobilization involved covalent attachment of the immobilization compound to the assay matrix. This was accomplished by contacting a solution or formulation of the compound(s) to be immobilized with a commercially available activated membrane or paper, such as Pall IMMUNODYNE® ABC, Gelman ULTRABIND® or Millipore IMMOBILON®, using procedures recommended by the manufacturer.

Alternatively, chemical activation of the hydroxyl-group-containing assay matrix (cellulose paper or membrane) can be performed by incubating a 20×25 cm sheet of membrane or paper in a covered baking dish 23×28 cm for 2 hours at room temperature in 500 mL of 0.2 M 1,1'-carbonyldiimidazole (CDI, Aldrich product no. 11,553-3). Following this incubation, the activated membrane is washed extensively in several (4-8) 250 mL volumes of methylene chloride and dried under nitrogen. This procedure results in activated membrane to which proteins or small molecules with primary amine functional groups can be covalently immobilized (non-diffusive binding). Non-diffusive-immobilization of the protein to the activated membrane, either prepared as outlined above or using one of the commercial activated membranes, is accomplished by incubating the activated membrane in 100 mL of a 0.01 mg/mL to 10 mg/mL solution of the desired immobilization compound in 0.1 M sodium phosphate, pH 7, at room temperature for two hours. The paper is then washed by incubation for 20 minutes in 500 mL of 0.1 M sodium phosphate pH 7. The washing step is repeated 4 times, then the paper is soaked in 150 mL of 0.5% polyvinyl alcohol (PVA, Aldrich 18,965-0) for 10 minutes, gently blotted and dried in a convection oven at 45° C. for 10 to 30 minutes or until dry.

Colloidal gold conjugates of mouse IgG, 1H11 (monoclonal anti-NTx), and NTx are commercially available from EY Laboratories, San Mateo, Calif. Methods for the preparation of colloidal gold conjugates are disclosed in Muller, C., et al., *J. Imm. Methods,* 37, 185-190 (1980); Roth, J., "Techniques in Immunicytochemistry," Academic Press, pp. 219-284. Conjugates include: Gold-1H11 (15 nm particle, monoclonal anti-NTx); Gold-Mouse IgG1 Kappa (15 nm particle); Gold-NTx (15 nm particles).

Preparation of latex particle conjugates accomplished by immobilizing NTx, NTx-protein conjugate, MAb-1H11 or Mouse IgG to 0.356 μm microspheres (Bangs stock #D0003561CB) to produce NTx-Latex, NTx-protein-latex and MAb 1H11-Latex conjugates. To a suspension of 0.356 μm carboxylated microspheres add 10 molar equivalents (relative to the COOH groups on the bead surface) of 1-ethyl-3-(dimethylaminopropyl)carbodiimide (EDAC, Sigma E 0388) and 10 molar equivalents of N-Hydroxysuccimimide (NHS, Pierce 24500) in 0.1 M sodium phosphate, pH 7.0, and 0.5% Tween 20 at room temperature with stirring for 30 minutes. Purify by centrifugation at 13,000 RPM for 15 minutes followed by washing with 10 mM sodium phosphate pH 7, 0.5% Tween 20. Add either the NTx, NTx-protein conjugate, or MAb-1H11 at a ten fold molar excess to a stirring solution of the activated microspheres in 0.1 M sodium phosphate, pH 7.0, 0.5% Tween 20, and allow to react for 2 hours at room temperature; then purify by centrifugation with washing and dialysis. The microparticles now have the desired immobilization compound non-diffusively immobilized.

Assay strips and reagents were prepared as discussed in the first strip preparation method and the first non-diffusive immobilization method above. The strips were either 0.5 cm wide by 6 cm long or 0.3 cm wide by 3 cm long, depending on the experiment. The following assay protocol was used:

1. Sample was added (25 μL-100 μL) to the bottom of a 12×75 mm test tube.
2. An assay strip (reagents already applied) was inserted into the test tube. Sufficient time was allowed for wicking to completely saturate the strip. This required about 5-8 minutes for the 0.5 cm×6 cm strips and about 1-3 minutes for the 0.3 cm by 3 cm strips.
3. The test zones on the assay strips were read with a Gretag model D182 reflectance densitometer.

EXAMPLE 2

This example demonstrates a single-step, quantitative, lateral flow, inhibition type immunoassay for a small molecule using colored particles as the detection method. The assay summarized below in Table 1 was conducted using reagents and methods as described in Example 1.

The assay strips of this example were 6 cm wide and 0.5 cm long and were similar to those shown in FIG. 1 and FIG. 3, with the exception that the third zone 18 (second test zone) was not included. The immunoassay strip configuration was as follows:
(1) a lower 8 μm pore size nitrocellulose section containing a reagent zone 14 having diffusively applied MAb-1H11-colloidal gold, prepared as described above;
(2) a 0.5 cm test zone 16 containing non-diffusively immobilized NTx covalently linked via the native primary amine group to Pall IMMUNODYNE® ABC, prepared as described above; and
(3) an upper wick area of 8 μm pore size nitrocellulose that extended from the upper edge of zone 16 to the top of the strip.

All strip zones were laminated in physical communication with adjacent zone(s), permitting fluid to flow through the entire strip by wicking action, and were supported on a plastic backing as outlined above.

NTx was diluted in PBS to the concentrations indicated in Table 1 below, and the general assay protocol of Example 1 was used to generate the data shown in Table 1. These data indicate a dose-response demonstrating good sensitivity and quantitative performance for the present invention. The assay results in Table 1 demonstrate that the present assay strip and method can distinguish a 1 nM concentration of the peptide marker NTx from the background (0 concentration) using colloidal gold as the signal reagent.

TABLE 1

NTx Dose Response
Conjugate: Colloidal Gold-1H11

| NTx (nM) | Reflectance Density (Gretag) |
|---|---|
| 0 | 0.60 |
| 1 | 0.57 |
| 30 | 0.55 |
| 100 | 0.52 |
| 300 | 0.41 |
| 1000 | 0.21 |
| 3000 | 0.18 |

EXAMPLE 3

This example demonstrates a quantitative, lateral flow, inhibition type immunoassay which shows excellent performance using colored particles as the indicator. The assay summarized below in Table 2 was conducted using strips, reagents and methods as described in Example 2.

The assay protocol as indicated above in Example 1 was used to generate data in the non-amplified data column of Table 2. For the silver amplified assays, the protocol was followed as in Example 1, with the exception that a silver enhancement reagent was added to the test zone after the colloidal gold binding. The results in Table 2 demonstrate a dose-response showing excellent sensitivity and quantitative performance for the present invention.

TABLE 2

NTx Dose Response Silver Amplification
Conjugate: Colloidal-Gold-1H11

| NTx (nM) | Reflectance Density Gretag | |
|---|---|---|
| | Non-Amplified | Silver-Amplified |
| 1 | 0.30 | 1.07 |
| 30 | 0.25 | 0.91 |
| 100 | 0.19 | 0.84 |
| 300 | 0.15 | 0.59 |
| 1000 | 0.09 | 0.23 |
| 3000 | 0.08 | 0.02 |

EXAMPLE 4

This example demonstrates a single-step, quantitative, lateral flow, competitive type immunoassay for a protein using colored particles as the indicator. The assay summarized below in Table 3 was conducted using reagents and methods as described in Example 1.

The assay strips of this example were 6 cm wide and 0.5 cm long and were similar to those shown in FIG. 1 and FIG. 3, with the exception that the first test zone (second zone 16) was not included. The immunoassay strip configuration was as follows:
(1) a lower 8 μm pore size nitrocellulose section containing continuous reagent zones 14 and 16, zone 14 having diffusively applied mouse IgG-colloidal gold, prepared as described above;
(2) a 0.5 cm test zone 18 containing non-diffusively immobilized goat anti-mouse adsorbed to 8 μm pore size nitrocellulose, prepared as described above; and
(3) an upper wick area of 8 μm pore size nitrocellulose that extended from the upper edge of zone 18 to the top of the strip.

All strip zones were laminated in physical communication with adjacent zone(s), permitting fluid to flow through the entire strip by wicking action, and were supported on a plastic backing as outlined above.

Mouse IgG was diluted in PBS to the concentrations indicated in Table 3 below, and the assay protocol of Example 1 was used to generate the data shown in Table 3. These data demonstrate a dose-response showing good sensitivity and quantitative performance for the present invention.

TABLE 3

IgG Dose Response
Conjugate: Colloidal Gold-IgG1

| Mouse IgG (μg/mL) | Reflectance Density (Gretag) |
|---|---|
| 0 | 0.13 |
| 8 | 0.10 |
| 33 | 0.09 |
| 50 | 0.08 |
| 100 | 0.06 |
| 200 | 0.05 |

EXAMPLE 5

This example demonstrates a single-step, quantitative, lateral flow, inhibition type immunoassay for a small molecule using colored particles as the indicator and an assay reference that is directly related to the assay function. The assay summarized below in Table 4 was conducted using reagents and methods described in Example 1.

The assay strips of this example were 6 cm wide and 0.5 cm long and are shown in FIG. 1 and FIG. 3. The immunoassay strip configuration was as follows:

(1) a lower 8 μm pore size nitrocellulose section containing a reagent zone 14 having diffusively applied MAb-1H11-colloidal gold, prepared as described above;

(2) a 0.5 cm test zone 16 containing non-diffusively immobilized NTx covalently linked via the native primary amine group to Pall IMMUNODYNE® ABC, prepared as described above;

(3) a 0.5 cm spacer 22 of 8 μm pore size nitrocellulose;

(4) a 0.5 cm long test zone 18 of 8 μm pore size nitrocellulose containing non-diffusively immobilized, adsorbed goat-anti-mouse; and (5) an upper wick area of 8 μm pore size nitrocellulose that extended from the upper edge of zone 18 to the top of the strip.

All strip zones were laminated in physical communication with adjacent zone(s), permitting fluid to flow through the entire strip by wicking action, and were supported on a plastic backing as outlined above.

NTx was diluted in PBS to the concentrations indicated in Table 4 below, and the general assay protocol of Example 1 was used to generate the data shown in Table 4. These data demonstrate a dose-response in both test zone 16 and test zone 18 showing good sensitivity and quantitative performance for the present invention. The sum of the two test zones remained substantially constant, thus indicating a correct functioning of the internal reference feature of the present invention, wherein the sum of the signal from test zone one and test zone two provides a reliable quality reference to assure correct assay performance.

TABLE 4

NTx Dose Response Two Test Zones
Conjugate: Colloidal Gold-1H11

| | Reflectance Density (Gretag) | | |
|---|---|---|---|
| NTx (nM) | TestZone 1 | TestZone 2 | Sum |
| 1 | 0.38 | 0.10 | 0.48 |
| 30 | 0.32 | 0.16 | 0.48 |
| 100 | 0.21 | 0.25 | 0.46 |
| 300 | 0.14 | 0.35 | 0.49 |
| 1000 | 0.09 | 0.40 | 0.49 |
| 3000 | 0.07 | 0.47 | 0.54 |

EXAMPLE 6

This example demonstrates a quantitative, lateral flow, inhibition type immunoassay for a small molecule using an enzyme label as the detection system. The assay summarized below in Table 5 was conducted using strips, reagents and methods as described in Example 2, with the exception that the lower reagent zone 14 contained diffusively applied HRP-1H11. Five μL of 0.1μ g/mL HRP-1H11 was applied to zone 14. As indicated in Table 5, an approximately 1.5 mg/mL solution of NTx-IgG conjugate was diluted 1:10, 1:20 and 1:40, then adsorbed as described in Example 1 to the 8 μm pore size nitrocellulose of test zone 16.

NTx was diluted in PBS to the concentrations indicated in Table 5 below, and the assay protocol of Example 1 was used to generate the data shown in Table 5. These data illustrate dose-responses at each of three different NTx immobilization conditions which show good sensitivity and quantitative performance for the present invention when an enzyme indicator is used.

TABLE 5

NTx Dose Response
Conjugate HRP-1H11 at 0.1 μg/mL
Various NTx-protein immobilization concentrations

| | NTx-Protein Dilution | | |
|---|---|---|---|
| NTx (nM) | 1:10 | 1:20 | 1:40 |
| | Reflectance Density (Gretag) | | |
| 24 | 0.47 | 0.49 | 0.52 |
| 80 | 0.41 | 0.40 | 0.42 |
| 240 | 0.32 | 0.38 | 0.30 |
| 800 | 0.27 | 0.27 | 0.20 |
| 2400 | 0.16 | 0.19 | 0.17 |

EXAMPLE 7

This example demonstrates a single-step, quantitative, lateral flow, competition-type immunoassay for a small molecule using colored particles as the indicator. The assay summarized below in Table 6 was conducted using reagents and methods as described in Example 1.

The assay strips of this example were 3 cm wide and 0.3 cm long, and were similar to those shown in FIG. 1 and FIG. 3, with the exception that the third zone 18 (second test zone) was not included. The immunoassay strip configuration was as follows:

(1) a lower 8 μm pore size nitrocellulose section containing continuous reagent zone 14 having diffusively immobilized NTx-latex beads (blue), prepared as described above;

(2) a 0.3 cm test zone 18 containing non-diffusively immobilized 1H11 monoclonal anti-NTx, adsorbed to 8 µm pore size nitrocellulose, prepared as described above; and (3) an upper wick area of 8 µm pore size nitrocellulose that extended from the upper edge of zone 16 to the top of the strip.

All strip zones were laminated in physical communication with adjacent zone(s), permitting fluid to flow through the entire strip by wicking action, and were supported on a plastic backing as outlined above.

NTx was diluted in PBS to the concentrations indicated in Table 6 below, and the general assay protocol of Example 1 was used to generate the data shown in Table 6. These data illustrate a dose-response demonstrating good sensitivity and quantitative performance for the present invention using blue latex particles as the signal reagent.

TABLE 6

NTx Dose Response
Conjugate: Latex Bead-NTx
1H11 Immobilized

| NTx (nM BCE) | Reflectance Density |
|---|---|
| 30 | 0.79 |
| 100 | 0.64 |
| 300 | 0.46 |
| 1000 | 0.33 |
| 3000 | 0.20 |

EXAMPLE 8

This example demonstrates a single-step, quantitative, lateral flow, competition-type immunoassay for a proteins using colored particles as the indicator. The assay summarized below in Table 7 was conducted using reagents and methods as described in Example 1. The assay strips of this example were 3 cm wide and 0.3 cm long, and were similar to those shown in FIG. 1 and FIG. 3, with the exception that the second zone 16 (first test zone) was not included. The immunoassay strip configuration was as follows:

(1) a lower 8 µm pore size nitrocellulose section, containing reagent zone 14 having diffusively applied mouse IgG-latex beads (blue);

(2) a 0.3 cm intermediate section of 8 µm pore size nitrocellulose, containing test zone 18 having non-diffusively immobilized goat anti-mouse adsorbed thereto; and (3) an upper wick area of 8 µm pore size nitrocellulose that extended from the upper edge of zone 18 to the top of the strip.

All strip zones were laminated in physical communication with adjacent zone(s), permitting fluid to flow through the entire strip by wicking action, and were supported on a plastic backing as outlined above.

Mouse IgG was diluted in PBS to the concentrations indicated in Table 7 below, and the general assay protocol of Example 1 was used to generate the data shown in Table 7. These data illustrate a dose-response demonstrating good sensitivity and quantitative performance for the present invention using blue latex particles as the signal reagent.

TABLE 7

IgG Dose Response
Conjugate: NTx-IgG-Latex Beads
Goat anti-mouse immobilized

| Mouse IgG (µg/mL) | Reflectance Density |
|---|---|
| 0 | 0.62 |
| 4 | 0.52 |
| 8 | 0.44 |
| 33 | 0.37 |
| 50 | 0.33 |
| 100 | 0.26 |
| 200 | 0.23 |

EXAMPLE 9

This example demonstrates a single-step, quantitative, lateral flow, competitive-type immunoassay for a small molecule and a large molecule, using colored particles as the indicator and an assay reference that is directly related to the assay function. The assay summarized below in Table 8 was conducted using reagents and methods as described in Example 1. The assay strips of this example were 3 cm wide and 0.3 cm long, and are shown in FIG. 1 and FIG. 3. The immunoassay strip configuration was as follows:

(1) a lower 8 µm pore size nitrocellulose section, containing reagent zone 14 having diffusively immobilized NTx-latex beads (0.412 µm, blue);

(2) a 0.3 cm intermediate section of 8 µm pore size nitrocellulose, containing test zone 18 having non-diffusively immobilized 1H11 monoclonal anti-NTx adsorbed thereto;

(3) a 0.5 cm spacer of 8 µm pore size nitrocellulose;

(4) a 0.3 cm long section of 8 µm pore size nitrocellulose, containing test zone 18 having non-diffusively immobilized goat-anti mouse adsorbed thereto; and (5) an upper wick area of 8 µm pore size nitrocellulose that extended from the upper edge of zone 18 to the top of the strip.

All strip zones were laminated in fluid communication with adjacent zone(s), permitting fluid to flow through the entire strip by wicking action, and were supported on a plastic backing as outlined above.

NTx was diluted in PBS to the concentrations indicated in Table 8, and the general assay protocol of Example 1 was used to generate the data shown in Table 8. These data illustrate a dose-response in both test zone 16 and test zone 18 demonstrating good sensitivity and quantitative performance for the present invention. The sum of the signals from the two test zones remains substantially constant throughout the NTx concentration range, indicating a correct functioning of the assay.

According to the present invention, the sum of the signals from test zones 16 and 18 provides an internal quality reference to assure reliable and correct assay performance. In addition, better assay sensitivity is seen in test zone 18 at the lower end of the curve (0 to 30 nM NTx), while better separation (sensitivity) is seen in test zone 16 at the upper end of the curve (100 to 300 nM NTx). These results suggest a that hybrid calibration algorithm using both test zones can provide improved performance, relative to previously described single-test-zone methods. According to the present invention, assay calibration and instrumental reading can use a single test zone alone, or both test zones either separately or combined, to provide maximum sensitivity and reliability.

TABLE 8

NTx Dose Response Two Test Zones
Conjugate: Latex Bead-NTx
Immobilized Zone 1-1H11, Zone 2-Goat Anti-Mouse

| NTx (nM) | Reflectance Density (Gretag) | | |
|---|---|---|---|
| | Zone 1 | Zone 2 | Sum |
| 0 | 1.01 | 0.23 | 1.24 |
| 1 | 1.06 | 0.21 | 1.27 |
| 30 | 1.05 | 0.40 | 1.45 |
| 100 | 0.96 | 0.50 | 1.46 |
| 300 | 0.68 | 0.57 | 1.25 |

EXAMPLE 10

The assay summarized below in Table 9 was conducted using strips, reagents and methods as described in Example 9, with the exception that monoclonal rat anti-mouse was immobilized in zone 18.

The conclusions of Example 9 are supported by these data.

TABLE 9

NTx Dose Response Two Test Zones
Conjugate: Latex Bead-NTx
Immobilized Zone 11H11, Zone 2 Monoclonal Rat-Anti-Mouse

| NTx (nM) | Reflectance Density (Gretag) | | |
|---|---|---|---|
| | Zone 1 | Zone 2 | Sum |
| 0 | 0.99 | 0.37 | 1.36 |
| 1 | 0.86 | 0.40 | 1.26 |
| 30 | 0.84 | 0.44 | 1.28 |
| 100 | 0.79 | 0.56 | 1.35 |
| 300 | 0.38 | 0.62 | 1.00 |

EXAMPLE 11

Figure 8:
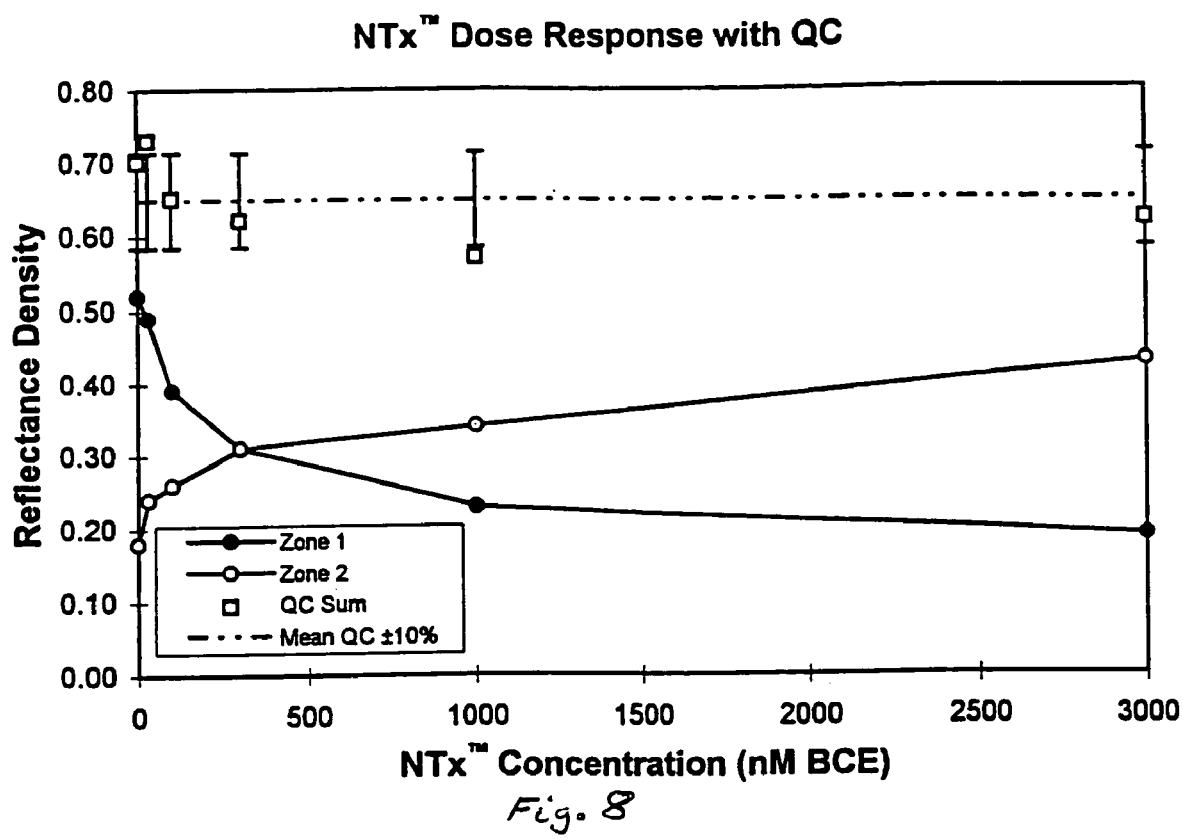
FIG. 8 is a graphical representation of a dose response to NTx with quality reference plotting reflectance density vs. NTx concentration.

The test results graphically represented in FIG. 8 were from an assay conducted using strips, reagents and methods as described in Example 9, except as otherwise noted. FIG. 8 illustrates the NTx dose response using IgG-C-peptide in the first test zone on nitrocellulose membrane, S&S AE 98, with a pore size of 5 um. The second test zone immobilized monoclonal rat anti-mouse on nitrocellulose.

Numerous modifications and variations of the present invention are possible in light of the above teachings. It is therefore to be understood that within the scope of the appended claims, the invention may be practiced otherwise than as specifically described herein.

What is claimed is:

1. A dry reagent lateral flow strip assay device for detecting at least one analyte in a test sample within a pre-determined range of analyte concentration using a porous member capable of being traversed by the sample comprising:
   a) a sample application zone on the porous member having diffusively immobilized therewith a labeled indicator reagent, which does not bind to the analyte;
   b) at least one test zone having non-diffusively bound thereto a pre-determined amount of a first reagent, based on the pre-determined range of analyte concentration, that that binds to both the labeled indicator reagent and to the analyte to produce a corresponding detectable response in the test zone, the pre-determined amount of the first reagent such that the detectable response is inversely proportional to the analyte concentration;
   c) at least one reference zone having non-diffusively bound thereto a pre-determined amount of a second reagent, based on the pre-determined range of analyte concentration, that binds to the labeled indicator reagent to produce corresponding detectable response in the reference zone, the pre-determined amount of the second reagent such that the detectable response is directly proportional to the analyte concentration;
   wherein the sample application zone, the test zone and the reference zone are in fluid communication with one another through the porous member; and
   wherein the detectable response in the test zone plus the detectable response in the reference zone equal a total detectable response that is substantially constant for the pre-determined range of analyte concentration.

2. The assay device of claim 1, wherein the porous member further comprises a bibulous solid phase material.

3. The assay device of claim 2, wherein the porous member further comprises fiberglass, cellulose or nylon.

4. The assay device of claim 1 for detecting multiple analytes in a test sample, further comprising more than one test zone, each corresponding to an analyte.

5. The assay device of claim 1, wherein the porous member further comprises more than one bibulous material, wherein the sample application zone, the test zone and the reference zone are in fluid communication therethrough.

6. The assay device of claim 1, further comprising one or more reagents bound to the porous member, the reagents being selected from the group consisting of: antibodies, antigens, enzymes, substrates, small molecules, proteins, viral lysate, bacterial lysate, receptors, sugars, carbohydrates, polymers and detergents.

7. The assay device of claim 1, further comprising a sample filtration member in contact with the porous member.

8. The assay device of claim 1, wherein the labeled indicator reagent is a particle-linked antigen or a particle linked antibody.

9. The assay device of claim 1, wherein the first reagent is an antibody or an antigen.

10. The assay device of claim 1, wherein the second reagent is an antibody that binds to the labeled indicator reagent to form the second reaction product.

* * * * *

UNITED STATES PATENT AND TRADEMARK OFFICE
CERTIFICATE OF CORRECTION

PATENT NO. : 7,635,597 B2
APPLICATION NO. : 10/826880
DATED : December 22, 2009
INVENTOR(S) : Blatt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 701 days.

Signed and Sealed this

Twenty-first Day of December, 2010

David J. Kappos
*Director of the United States Patent and Trademark Office*